United States Patent [19]
Geczy et al.

[11] Patent Number: 5,731,166
[45] Date of Patent: Mar. 24, 1998

[54] RECOMBINANT PRODUCTION OF CHEMOTACTIC CP-10 POLYPEPTIDES AND THERAPEUTIC METHODS USING THEM

[75] Inventors: Carolyn Geczy, Greenwich; Richard John Simpson, Richmond; Martin Lackmann, Newport, all of Australia

[73] Assignee: The Heart Research Institute Ltd., Campberdown, Australia

[21] Appl. No.: 987,272

[22] PCT Filed: Sep. 5, 1991

[86] PCT No.: PCT/AU91/00410

§ 371 Date: Apr. 23, 1993

§ 102(e) Date: Apr. 23, 1993

[87] PCT Pub. No.: WO92/04376

PCT Pub. Date: Mar. 19, 1992

[30] Foreign Application Priority Data

Sep. 5, 1990 [AU] Australia ................... PK2127
Feb. 5, 1991 [AU] Australia ................... PK4463

[51] Int. Cl.⁶ .................... C07K 14/52; C12N 15/19
[52] U.S. Cl. ............ 435/69.1; 536/23.5; 536/24.31; 530/350; 530/351; 530/413; 435/320.1; 435/325; 435/252.3; 435/254.11; 514/2
[58] Field of Search .................... 530/395, 413, 530/351, 350; 514/8, 2; 536/23.5, 24.31; 435/320.1, 240.2, 69.1, 325, 252.3, 254.11; 424/85.1

[56] References Cited

FOREIGN PATENT DOCUMENTS

WO9007863  7/1990  WIPO.

OTHER PUBLICATIONS

Chemical Abstracts, vol. 109, No. 19, Nov. 1988, Ryan, Janes et al: "Macrophage procoagulant–inducing factor. In vivo properties and chemotactic activity for phagocytic cells". pp 570.

Chemical Abstracts, Nol 111, Nol 21, Nov. 1989: Yoshizuka, Naonobu et al: "Macrophage chemotactic factor (MCF) produced by a human T cell hybridoma clone". pp. 598.

Bildau, H., et al (1989) *Exp. Cell Biology*, 57 (2): p. 123, abst. No. 94.

Lackmann, M., et al., *J. Biol. Chem.* 267: 7499–7904, 1992.

Lackmann, M. et al., *J. Immunol.* 150: 2981–91, 1993.

Lagasse et al., *Mol. Cell. Biol.* 8: 2402–10, 1988.

Lagasse, E., et al., *Blood* 79: 1907–15, 1992.

Odink, K., et al., *Nature* 330: 80–82, 1987.

Ryan, J., et al., *J. Immunol.* 141: 2110–17, 1988.

Ryan, J., et al., *Immunol. Cell Biol.* 65: 127–39, 1987.

Sambrook, J., et al., *Molecular Cloning*, 2d. ed. Chapter 11, 1989 [selected pages provided].

*Primary Examiner*—David L. Fitzgerald
*Attorney, Agent, or Firm*—Cushman Darby & Cushman Intellectual Property Group of Pillsbury Madison & Sutro LLP

[57] ABSTRACT

The chemotactic protein CP-10, in essentially pure form, having an apparent molecular weight of approximately 10 kD and having chemotactic activity for neutrophils, monocytes/macrophages and/or other mammalian cells, or an analogue, mutant, fragment, derivative or functional homologue of CP-10. Amino acid and nucleotide sequences for CP-10 are disclosed, as well as production and use thereof.

29 Claims, 13 Drawing Sheets

```
GAP OF: mCP10.seq    FROM: 1  TO: 433
        CDNA SEQUENCE FROM AJ
TO:   humMRP8.seq    FROM: 1  TO: 448
      LOCUS     HUMMRP8    418 bp ss-mRNA GAP WEIGHT:    3.000     AVERAGE MATCH:     1.000
LENGTH WEIGHT: 0.100     AVERAGE MISMATCH:  0.000

QUALITY: 258.1                    LENGTH: 486
RATIO:   0.596                    GAPS:     5
PERCENT SIMILARITY: 69.620    PERCENT IDENTITY: 69.620 mCP10.seq x humMRP8.seq

1  ..........................GAATTCCCCGTCT       13 mCP10
                             ||||    ||||||
1  .................ATGTCTCTTGTCAGCTGTCT         20 hMRP8
                          M  S  E

14 TCAATGCGACATCGTTTGAAAGGAAATCTTTCGTGACAATGCCGTCTGAA  63 mCP10
   ||  |||| |  ||||| |     ||||||  |||| |||| ||| ||||
21 TTCAGAAGACCTGGTGGGGCA..AGTTCCGTGGGCATCATGTTGACCGAG  68 hMRP8
     M  L  T  E
```

```
          L  E  K  A  L  S  N  L  I  D  V  Y  H  N  Y  S  N
 64  CTGGAGAAGGCCTTGAGCAACCTCATTGATGTCTACCACAATTATTCCAA  113  mCP10
     |||||| ||||||  |||||||| |||||| ||| | ||   ||  |
 69  CTGGAGAAAGCCCTTGAACTTCATCGACGTCTACCAAGTACTCCCT       118  hMRP8
          L  E  K  A  L  N  L  I  D  V  H  K  Y  S  L

I  Q  G  N  H  H  A  L  Y  K  N  D  F  K  K  M
114  TATACAAGGAAATCACCATGCCCTCTACAAGAATGACTTCAAGAAAATGG  163  mCP10
     |  |  ||||| ||  |||||  ||| || |||| |||||| |||||
119  GATAAAGGGGAATTTCCATGCCGTCTACAGGGATGACCTGAAGAAATTGC  168  hMRP8
          I  K  G  N  F  H  A  V  Y  R  D  D  L  K  K  L

V  T  T  E  C  P  Q  F  V  Q  N  I  N  I  E  N  L
164  TCACTACTGAGTGTCCTCAGTTTGTGCAGAATATAAATATCGAAAACTTG  213  mCP10
      |  ||| || || ||||| ||| | |||  |   ||  |||
169  TAGAGACCGAGTGTCCTCAGTATCAGGAAAAAGGGGTGCAGACGTCTGG   218  hMRP8
          L  E  T  E  C  P  Q  Y  I  R  K  K  G  A  D  V  W
```

UPPER CASE – PROPOSED SEQUENCE
LOWER CASE – IDENTIFICATION BY EDMAN DEGRADATION

FIG. 8

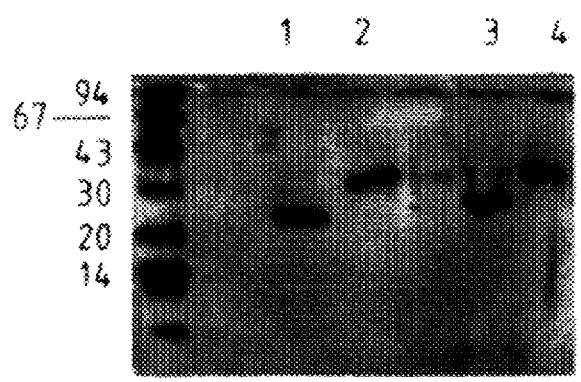
FIG. II

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 88 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Pro Ser Glu Leu Glu Lys Ala Leu Ser Asn Leu Ile Asp Val Tyr His
 1               5                  10                  15

Asn Tyr Ser Asn Ile Gln Gly Asn His His Ala Leu Tyr Lys Asn Asp
            20                  25                  30

Phe Lys Lys Met Val Thr Thr Glu Cys Pro Gln Phe Val Gln Asn Ile
        35                  40                  45

Asn Ile Glu Asn Leu Phe Arg Glu Leu Asp Ile Asn Ser Asp Asn Ala
    50                  55                  60

Ile Asn Phe Glu Glu Phe Leu Ala Met Val Ile Lys Val Gly Val Ala
65                  70                  75                  80

Ser His Lys Asp Ser His Lys Glu
                    85
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Pro Gln Phe Val Gln Asn Ile Asn Ile Glu Asn Leu Phe Arg
 1               5                  10
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Pro Gln Phe Val Gln Asn Ile Asn Ile Glu Asn Leu Phe Arg Tyr
 1               5                  10                  15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Pro Gln Phe Val Gln Asn Ile Asn Ile Glu Asn Leu Phe Arg Tyr
 1               5                  10                  15
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ala Ser His Lys Asp Ser His Lys Glu
 1               5
```

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ala Ala His Lys Lys Ser His Glu Glu Ser His Lys Glu
 1               5                   10
```

( 2 ) INFORMATION FOR SEQ ID NO:7:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Met Leu Thr Glu Leu Glu Lys Ala Leu Asn Ser Ile Ile Asp Val Tyr
 1               5                  10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
                35                  40                  45

Lys Gly Ala Asp Val Trp Phe Lys Glu Leu Asp Ile Asn Thr Asp Gly
        50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```

( 2 ) INFORMATION FOR SEQ ID NO:8:

( i ) SEQUENCE CHARACTERISTICS:
  ( A ) LENGTH: 109 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:8:

```
Ser Gln Leu Glu Arg Asn Ile Glu Thr Ile Ile Asn Thr Phe His Gln
 1               5                  10                  15

Tyr Ser Val Lys Leu Gly His Pro Asp Thr Leu Asn Gln Gly Glu Phe
            20                  25                  30

Lys Glu Leu Val Arg Lys Asp Leu Gln Asn Phe Leu Lys Lys Glu Asn
            35                  40                  45

Lys Asn Glu Leu Val Ile Glu His Ile Met Glu Asp Leu Asp Thr Asn
         50                  55                  60

Ala Asp Lys Gln Leu Ser Phe Glu Glu Phe Ile Met Leu Met Ala Arg
 65                  70                  75                  80

Leu Thr Trp Ala Ser His Glu Lys Met His Glu Gly Asp Glu Gly Pro
                     85                  90                  95

Gly His His His Lys Pro Gly Leu Gly Glu Gly Thr Pro
                 100                 105
```

( 2 ) INFORMATION FOR SEQ ID NO:9:

( i ) SEQUENCE CHARACTERISTICS:
  ( A ) LENGTH: 95 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:9:

```
Pro Ser Gln Met Glu His Ala Met Glu Thr Met Met Phe Thr Phe His
 1               5                  10                  15

Lys Phe Ala Gly Asp Lys Gly Tyr Leu Thr Lys Glu Asp Leu Arg Val
            20                  25                  30

Leu Met Glu Lys Glu Phe Pro Gly Phe Leu Glu Asn Gln Lys Asp Pro
            35                  40                  45

Leu Ala Val Asp Lys Ile Met Lys Asp Leu Asp Gln Cys Arg Asp Gly
         50                  55                  60

Lys Val Gly Phe Gln Ser Phe Phe Ser Leu Ile Ala Gly Leu Thr Ile
 65                  70                  75                  80

Ala Cys Asn Asp Tyr Phe Val Val His Met Lys Gln Lys Gly Lys
                     85                  90                  95
```

( 2 ) INFORMATION FOR SEQ ID NO:10:

( i ) SEQUENCE CHARACTERISTICS:
  ( A ) LENGTH: 89 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:10:

```
Ala Cys Pro Leu Asp Gln Ala Ile Gly Leu Leu Val Ala Ile Phe His
 1               5                  10                  15

Lys Tyr Ser Gly Arg Glu Gly Asp Lys His Thr Leu Ser Lys Lys Glu
```

```
                    20                      25                       30
     Leu  Lys  Glu  Leu  Ile  Gln  Lys  Glu  Leu  Thr  Ile  Gly  Ser  Lys  Leu  Gln
               35                      40                      45

Asp  Ala  Glu  Ile  Ala  Arg  Leu  Met  Glu  Asp  Leu  Asp  Arg  Asn  Lys  Asp
          50                      55                      60

Gln  Glu  Val  Asn  Phe  Gln  Glu  Tyr  Val  Thr  Phe  Leu  Gly  Ala  Leu  Ala
     65                      70                      75                      80

Leu  Ile  Tyr  Asn  Glu  Ala  Leu  Lys  Gly
                    85
```

(2) INFORMATION FOR SEQ ID NO:11:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
     Ser  Glu  Leu  Glu  Lys  Ala  Met  Val  Ala  Leu  Ile  Asp  Val  Phe  His  Gln
     1              5                       10                      15

Tyr  Ser  Gly  Arg  Glu  Gly  Asp  Lys  His  Lys  Leu  Lys  Lys  Ser  Glu  Leu
                    20                      25                      30

Lys  Glu  Leu  Ile  Asn  Asn  Glu  Leu  Ser  His  Phe  Leu  Glu  Glu  Ile  Lys
               35                      40                      45

Glu  Gln  Glu  Val  Val  Asp  Lys  Val  Met  Glu  Thr  Leu  Asp  Asn  Asp  Gly
          50                      55                      60

Asp  Gly  Glu  Cys  Asp  Phe  Gln  Glu  Phe  Met  Ala  Phe  Val  Ala  Met  Val
     65                      70                      75                      80

Thr  Thr  Ala  Cys  His  Glu  Phe  Phe  Glu  His  Glu
                    85                      90
```

(2) INFORMATION FOR SEQ ID NO:12:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
     Lys  Ser  Pro  Glu  Glu  Leu  Lys  Gly  Ile  Phe  Glu  Lys  Tyr  Ala  Ala  Lys
     1              5                       10                      15

Glu  Gly  Asp  Pro  Asn  Gln  Leu  Ser  Lys  Glu  Glu  Leu  Lys  Leu  Leu  Leu
                    20                      25                      30

Gln  Thr  Glu  Phe  Pro  Ser  Leu  Leu  Lys  Gly  Pro  Ser  Thr  Leu  Asp  Glu
               35                      40                      45

Leu  Phe  Glu  Glu  Leu  Asp  Lys  Asn  Gly  Asp  Gly  Glu  Val  Ser  Phe  Glu
          50                      55                      60

Glu  Phe  Gln  Val  Leu  Val  Lys  Lys  Ile  Ser  Gln
     65                      70                      75
```

(2) INFORMATION FOR SEQ ID NO:13:

(i) SEQUENCE CHARACTERISTICS:
        (A) LENGTH: 433 base pairs
        (B) TYPE: nucleic acid
        (C) STRANDEDNESS: single ( D ) TOPOLOGY: linear ( i i ) MOLECULE TYPE: cDNA to mRNA ( i x ) FEATURE:
    ( A ) NAME/KEY: CDS
    ( B ) LOCATION: 52..318

( x i ) SEQUENCE DESCRIPTION: SEQ ID NO:13:

```
GAATTCCCCG TCTTCAATGC GACATCGTTT GAAAGGAAAT CTTTCGTGAC A ATG CCG        57
                                                          Met Pro
                                                          1

TCT GAA CTG GAG AAG GCC TTG AGC AAC CTC ATT GAT GTC TAC CAC AAT       105
Ser Glu Leu Glu Lys Ala Leu Ser Asn Leu Ile Asp Val Tyr His Asn
        5                  10                  15

TAT TCC AAT ATA CAA GGA AAT CAC CAT GCC CTC TAC AAG AAT GAC TTC       153
Tyr Ser Asn Ile Gln Gly Asn His His Ala Leu Tyr Lys Asn Asp Phe
        20                  25                  30

AAG AAA ATG GTC ACT ACT GAG TGT CCT CAG TTT GTG CAG AAT ATA AAT       201
Lys Lys Met Val Thr Thr Glu Cys Pro Gln Phe Val Gln Asn Ile Asn
35                  40                  45                  50

ATC GAA AAC TTG TTC AGA GAA TTG GAC ATC AAT AGT GAC AAT GCA ATT       249
Ile Glu Asn Leu Phe Arg Glu Leu Asp Ile Asn Ser Asp Asn Ala Ile
                55                  60                  65

AAC TTC GAG GAG TTC CTT GCG ATG GTG ATA AAA GTG GGT GTG GCA TCT       297
Asn Phe Glu Glu Phe Leu Ala Met Val Ile Lys Val Gly Val Ala Ser
        70                  75                  80

CAC AAA GAC AGC CAC AAG GAG TAGCAGAGCT TCTGGCCTAG GGCTGGGTCC          348
His Lys Asp Ser His Lys Glu
            85

CTGGATATGT CTACAGAATA AAGTCATCAT ATCTCAGGTC AAAAAAAAAA AAAAAAAAA      408

AAAAAAAAAA AAAAAAAAGG AATTC                                           433
```

( 2 ) INFORMATION FOR SEQ ID NO:14:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Pro Ser Glu Leu Glu Lys Ala Leu Ser Asn Leu Ile Asp Val Tyr
1               5                   10                  15

His Asn Tyr Ser Asn Ile Gln Gly Asn His His Ala Leu Tyr Lys Asn
            20                  25                  30

Asp Phe Lys Lys Met Val Thr Thr Glu Cys Pro Gln Phe Val Gln Asn
        35                  40                  45

Ile Asn Ile Glu Asn Leu Phe Arg Glu Leu Asp Ile Asn Ser Asp Asn
    50                  55                  60

Ala Ile Asn Phe Glu Glu Phe Leu Ala Met Val Ile Lys Val Gly Val
65                  70                  75                  80

Ala Ser His Lys Asp Ser His Lys Glu
            85
```

( 2 ) INFORMATION FOR SEQ ID NO:15:

( i ) SEQUENCE CHARACTERISTICS:
        ( A ) LENGTH: 418 base pairs
        ( B ) TYPE: nucleic acid
        ( C ) STRANDEDNESS: single ( D ) TOPOLOGY: linear ( i i ) MOLECULE TYPE: cDNA to mRNA ( i x ) FEATURE:
    ( A ) NAME/KEY: CDS
    ( B ) LOCATION: 57..218

( i x ) FEATURE:
    ( A ) NAME/KEY: CDS
    ( B ) LOCATION: 57..335

( x i ) SEQUENCE DESCRIPTION: SEQ ID NO:15:

```
ATGTCTCTTG TCAGCTGTCT TTCAGAAGAC CTGGTGGGGC AAGTTCCGTG GGCATC                    56

ATG TTG ACC GAG CTG GAG AAA GCC TTG AAC TCT ATC ATC GAC GTC TAC                 104
Met Leu Thr Glu Leu Glu Lys Ala Leu Asn Ser Ile Ile Asp Val Tyr
 1               5                  10                  15

CAC AAG TAC TCC CTG ATA AAG GGG AAT TTC CAT GCC GTC TAC AGG GAT                 152
His Lys Tyr Ser Leu Ile Lys Gly Asn Phe His Ala Val Tyr Arg Asp
                20                  25                  30

GAC CTG AAG AAA TTG CTA GAG ACC GAG TGT CCT CAG TAT ATC AGG AAA                 200
Asp Leu Lys Lys Leu Leu Glu Thr Glu Cys Pro Gln Tyr Ile Arg Lys
            35                  40                  45

AAG GGT GCA GAC GTC TGG TTC AAA GAG TTG GAT ATC AAC ACT GAT GGT                 248
Lys Gly Ala Asp Val Trp Phe Lys Glu Leu Asp Ile Asn Thr Asp Gly
        50                  55                  60

GCA GTT AAC TTC CAG GAG TTC CTC ATT CTG GTG ATA AAG ATG GGC GTG                 296
Ala Val Asn Phe Gln Glu Phe Leu Ile Leu Val Ile Lys Met Gly Val
 65                  70                  75                  80

GCA GCC CAC AAA AAA AGC CAT GAA GAA AGC CAC AAA GAG TAGCTGAGTT                  345
Ala Ala His Lys Lys Ser His Glu Glu Ser His Lys Glu
                85                  90

ACTGGGCCCA GAGGCTGGGC CCTGGACAT GTACCTGCAG AATAATAAAG TCATCAATAC                405

CTCAAAAAAA AAA                                                                  418
```

( 2 ) INFORMATION FOR SEQ ID NO:16:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Leu Thr Glu Leu Glu Lys Ala Leu Asn Ser Ile Ile Asp Val Tyr
 1               5                  10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60

Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                85                  90
```

( 2 ) INFORMATION FOR SEQ ID NO:17:

( i ) SEQUENCE CHARACTERISTICS:
        ( A ) LENGTH: 76 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:17:

Pro Ser Glu Leu Glu Lys Ala Leu Ser Asn Leu Ile Asp Val Tyr His
1               5                   10                  15

Asn Tyr Ser Asn Ile Gln Gly Asn His His Ala Leu Tyr Lys Asn Asp
            20                  25                  30

Phe Lys Lys Met Val Thr Thr Glu Cys Pro Gln Phe Val Gln Asn Ile
        35                  40                  45

Asn Ile Glu Asn Leu Phe Arg Glu Leu Asp Ile Asn Ser Asp Asn Ala
    50                  55                  60

Ile Asn Phe Glu Glu Phe Leu Ala Met Val Ile Lys
65                  70                  75

( 2 ) INFORMATION FOR SEQ ID NO:18:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:18:

Pro Ser Glu Leu Glu Lys Ala Leu Ser Asn Leu Ile Asp Val Tyr His
1               5                   10                  15

Asn Tyr Ser Asn Ile Gln Gly Asn His His Ala Leu Tyr Lys Asn Asp
            20                  25                  30

Phe Lys Lys Met Val Thr
        35

( 2 ) INFORMATION FOR SEQ ID NO:19:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

Ala Leu Ser Asn Leu Ile Asp Val Tyr His Asn Tyr Ser Asn Ile Gln
1               5                   10                  15

Gly Asn His His Ala Leu Tyr Lys
            20

( 2 ) INFORMATION FOR SEQ ID NO:20:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

Pro Ser Glu Leu Glu Lys Ala Leu Ser Asn Leu Ile Asp Val Tyr His
1               5                   10                  15

Asn Tyr Ser Asn Ile Gln

-continued

20

( 2 ) INFORMATION FOR SEQ ID NO:21:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Met Val Thr Thr Glu Cys Pro Gln Phe Val Gln Asn Ile Asn Ile Glu
1               5                   10                  15
Asn Leu Phe Arg Glu Leu Asp Ile Asn
            20              25
```

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Val Thr Thr Glu Cys Pro Gln Phe Val Gln Asn Ile Asn Ile Glu Asn
1               5                   10                  15
Leu Phe Arg Glu Leu
            20
```

( 2 ) INFORMATION FOR SEQ ID NO:23:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Ser Asp Asn Ala Ile Asn Phe Glu Glu Phe Leu Ala Met Val Ile Lys
1               5                   10                  15
```

RECOMBINANT PRODUCTION OF CHEMOTACTIC CP-10 POLYPEPTIDES AND THERAPEUTIC METHODS USING THEM

This invention relates to a novel chemotactic factor, to the purification and characterisation of this factor from natural sources, and to the preparation of this factor as a synthetic or recombinant product. The invention further extends to analogues of the novel chemotactic factor, as well as to mutants, fragments and derivatives thereof. The invention also extends to antibodies to this factor (both polyclonal and monoclonal), to pharmaceutical compositions comprising the factor or the antibodies thereto, and to the therapeutic or diagnostic use of the factor or the antibodies thereto.

Leukocyte recruitment is vital for most inflammatory and immunologically-mediated responses. Chemotactic factors (CFs) released locally mediate directed migration of leukocytes and thus play an important role in the accumulation of these cells. Numerous CFs have been described including activated complement components (C5a, C3b), products of the activated coagulation cascade (kinins, thrombin, fibrinopeptides), bacterial and viral products, products of platelets, fibroblasts and neutrophils as well as the low molecular weight mediators leukotriene B4 and platelet activating factor (PAF) (reviews 1,2).

The delayed-type hypersensitivity (DTH) reaction is a widely studied example of cellular immunity. It is charcterised by accumulation, over 4–48 hr. of leukocytes at the site of intradermally-injected antigen in a sensitised subject. Polymorphonuclear leukocytes (PMNs) and monocytes are dominant in the lesion. The development of the reaction is considered to be due to the integrated release of numerous cytokines which not only control blood flow and vascular permeability but also determine the composition of the inflammatory infiltrate. It has been suggested that there may be a selective advantage in having a variety of factors (as evidenced by the number of CFs with activity towards, for example, PMNs) released under specific conditions and acting in particular micro-environments (3). Furthermore, the leukocyte composition of the inflammatory infiltrate depends on the temporal stage of the lesion and the nature of the stimulus. Thus activated lymphocytes may produce factors which are distinct from those derived from monocytes. Ward et. al. (4) and Altman (5) originally described the induction of CF when antigen was added to sensitised lymphocytes and the activity was attributed to a 12.5 kD protein (called lymphocyte-derived CF:LDCF). LDCF appears at the site of antigen challenge prior to macrophage influx (6) and has been extracted from DTH lesions (7). Miura et. al. (8) showed that activated Lyt 1+2–T lymphocytes from murine spleen were primarily responsible for the production of a macrophage CF but this factor has not been characterised and its relationship to the recently-described interleukin 8 family of monocyte-derived CFs (reviews 3,9) is unknown.

It has been previously proposed that fibrin, formed as a consequence of activated cell-mediated immunity (CMI), may enmesh infiltrating macrophages and maintain them at the inflammatory site (10). The generation of procoagulant by human monocytes reacting with microbial antigens is a close in vitro correlate of DTH reactions in man (11) and parallels the capacity of different mouse strains to develop DTH (12). Studies suggest that fibrin deposition at extravascular sites is mediated by macrophage procoagulant activity induced by an apparently unique T-cell derived product, macrophage procoagulant inducing factor (MPIF; 13–15).

Preliminary studies describing the characterisation of murine MPIF indicated activity associated with two heparin-binding peptides ($\alpha$ and $\beta$) with pIs of 8.5 and 9.0 respectively (14). On the basis of studies with other recombinant cytokines, depletion of activity with antibodies (Ab) to some cytokines and a variety of bioassays, MPIF was proposed to be a newly described factor. Furthermore, chromatographic fractions highly enriched for MPIF induced strong responses characterised by an intense infiltrate of PMNs after 4 hrs and of both PMNs and mononuclear cells after 24 hr when injected intradermally into rat skin. In addition, skin section showed significant interstitial fibrin deposition at 4 hr with maximal deposition at 24 hr post injection (15,16). The histopathological changes induced by MPIF$\alpha\beta$ were reminiscent of those described for skin reactive factor, a poorly characterised factor (17) distinct from macrophage migration inhibition factor (MIF) (18) which provokes DTH-like reactions when injected into normal skin. These results, also confirmed by in vitro experiments, indicated that a chemotactic activity was associated with MPIF$\alpha\beta$(16), thereby suggesting multiple biological functions of MPIF.

It has now been discovered that MPIF is distinct from a chemotactic cytokine contained in the MPIF preparation previously described, and in one aspect the present invention relates to the purification and characterisation of the chemotactic factor.

Proteases appear to play a central role in chemotaxis. They are implicated in the generation of chemotactic factors derived from extracts of DTH reactions from guineapig skin (25,26), and serine proteases are apparently important in chemotaxis of neutrophils and macrophages (27,28), particularly along a substream (29). It has been suggested that proteases bound to macrophages may cleave lymphocyte-derived CF precursor resulting in its activation (30). It has also been shown that chemotaxis of neutrophils in response to complement fragments or bacterial factors involves activation of a cell-bound serine esterase which apparently exists as a proenzyme and which is activated by chemotaxis. Heparin inhibits some types of chemotaxis and may act by suppressing the protease activity (31).

Accordingly, one aspect of the present invention is directed to a mammalian peptide having chemotactic properties, and having an apparent molecular weight of approximately 10 kD. The peptide of the present invention has chemotactic activity for neutrophils, monocytes/macrophages and/or other mammalian cells and also has apparent proteolytic activity which appears to play a role in leukocyte chemotaxis.

The peptide of this invention is referred to herein as chemotactic protein CP-10. It is to be understood, however, that the present invention extends to all analogues, mutants, fragments, derivatives, and functional homologues of CP-10 and to CP-10 molecules from all mammals such as from mice, humans and livestock animals. Use, thereof, of the term "CP-10" is meant to encompass all such forms of the molecule including single or multiple amino acid deletions, substitutions and insertions of associated molecules such as carbohydrates, lipids or other peptides. All CP-10 molecules and derivatives, mutants, fragments and/or functional homologues thereof may be prepared by recombinant or chemical synthesis or may be naturally occurring.

The purification of CP-10 form a MPIF preparation, and in particular the purification of murine CP-10 from a murine MPIF preparation, is described in detail herein. In general terms, a solution containing the chemotactic factor may be purified by chromatography and affinity procedures and the desired compound isolated and, if required, fragments or derivatives prepared therefrom. The chemotactic peptide of this aspect of the invention may be purified from any solution containing the peptide, including cell-extracts, pre-purified cell extract, cell supernatant or culture filtrate of stimulated lymphoid cells or other mammalian cells or of permanent cell lines. The purification procedures used may in general be selected from ion exchange chromatography, hydrophobic interaction chromatography, gel filtration chromatography, reversed phase chromatography or affinity chromatography employing heparin, $Cu^{2+}$, $Zn^{2+}$ or antibodies to CP-10 or any combinations thereof using open or high performance liquid chromatography systems. By appropriate purification methods, the chemotactic peptide of this invention, particularly murine CP-10, has now been obtained in essentially pure form.

N-terminal sequence analysis of the intact CP-10 molecule and tryptic and cyanogen bromide peptide has yielded a partial sequence with no potential glycosylation sites. By combining this partial N-terminal sequence with new data obtained by cDNA sequencing, the full length amino acid sequence of murine CP-10 has been determined to be SEQ ID NO: 1.

| 1. | $Ile^{12}$—$Tyr^{18}$ | |
| 2. | $Tyr^{29}$—$Met^{36}$ | |
| 3. | $Gln^{46}$—$Asn^{52}$ | (See Fig.1) |

Positive clones reacting with all 3 probes were identified from a cDNA library from activated spleen cells with A/J mice in the vector γgt 10 by in situ plaque hybridisation. Re-screening at low plaque density with probe 3 (probe No. 3 corresponds to the "hinge" or variant region) allowed selection of 2 positive clones. Probes 1 and 2 are prepared according to the amino acid sequences in the highly conserved regions of CP-10 and CFa/MRP8 in the N-terminal portion of the molecules. Results indicate that the cDNA library contains sequences coding form the murine equivalent of CFa/MRP8 in the N-terminal region of the molecule which are similar to those coding for CP-10. In addition, sequence coding for the "hinge" regions of CFa/MRP8 (probe 4) and CP-10 (probe 3) indicate that the proteins have distinct difference.

Pro — Ser — Glu — Leu — Glu — Lys — Ala — Leu — Ser — Asn — Leu — Ile — Asp — Val — Tyr — His — Asn — Tyr —
Ser — Asn — Ile — Gln — Gly — Asn — His — His — Ala — Leu — Tyr — Lys — Asn — Asp — Phe — Lys — Lys — Met —
Val — Thr — Glu — Cys — Pro — Gln — Phe — Val — Gln — Asn — Ile — Asn — Ile — Glu — Asn — Leu — Phe —
Arg — Glu — Leu — Asp — Ile — Asn — Ser — Asp — Asn — Ala — Ile — Asn — Phe — Glu — Glu — Phe — Leu — Ala —
Met — Val — Ile — Lys — Val — Gly — Val — Ala — Ser — His — Lys — Asp — Ser — His — Lys — Glu

The calculated molecular weight of full length murine CP-10 has been determined to be 10,163 D and the isoelectric point has been determined to be approx. 5.5.

No apparent amino acid sequence similarity is apparent with other CFs, interleukins, CSFs, interferons or tumor necrosis factors. Approx. 50% amino acid sequence similarity of CP-10 with two human calcium-binding proteins (CaBPs) recently identified in cells of myeloid origin and variously referred to as the cystic fibrosis (C.F.) antigen (19), MRP-8 or P8 and, MRP14 or P14 (20,21) respectively, is evident (see FIG. 1A–B and Australian Patent Application No. 79309/87). The full length sequence of murine CP-10 reveals 69.9% homology with MRPs at the cDNA level and 54.8% homology at the amino acid level (FIG. 1A–B). These proteins are members of a family of highly conserved CaBPs of low molecular weight (all approx. 10 kD) including S-100 α and β proteins, calcyclin and intestinal CaBP (review 22). None of the S-100-related proteins contains a signal sequence but a conserved hydrophobic domain present in the N terminus of all the proteins (including CP-10) may function as an internal signal sequence. Little is known about the function of MRP8 and 14; both are expressed in circulating neutrophils and monocytes but not in normal tissue macrophages (21,23). In chronic inflammatory conditions such as rheumatoid arthritis however, macrophages in affected tissues express both MRP8 and 14 whereas in acute inflammatory lesions only MPR14 is expressed (21). These proteins are also present in high levels in serum from cystic fibrosis patients (24). Interestingly, MRP8 and 14 were isolated from cultures of stimulated human mononuclear cells as part of a complex using a MAb directed against human MIF (21). However neither protein has MIF activity and their true biological function is unknown although by analogy with calmodulin they may be involved in intracellular signalling.

CP-10 of the present invention has also been shown to be a unique chemotactic factor on the basis of the following further experimental evidence. $^{32}$P-labelled oligonucleotide probes complementary to the mRNA of CP-10 were chemically synthesized based on the amino acid sequence of:

Earlier studies showed that in vivo skin reactions elicited with guinea pig skin reactive factor (probably related to CP-10) was suppressed by serine protease inhibitors and implicated involvement of proteolytic activity in cell recruitment in DTH reactions (32). Chemotactic activity of CP-10 is inhibited by heparin and heparin fragments with high affinity for antithrombin III. Although CP-10 is a heparin-binding protein, it is not yet known whether heparin inhibits via direct binding to CP-10 or by interacting with a cell membrane component essential for chemotaxis. It is suggested that CP-10 has proteolytic activity and that this activity plays a role in leukocyte chemotaxis.

Because of its chemotactic activity, CP-10 or its analogues, or CP-10-derived peptides with chemotactic activity may be useful if administered locally (e.g. around a tumor, site of infection) to attract neutrophils and/or monocytes to the site, particularly in immuno-compromised patients (i.e. those with sever combined immunodeficiencies, AIDS, tumors, burns etc.) or any patient who is allergic to skin test antigens (Type IV hypersenstivity).

In addition, CP-10 may contribute to inflammatory pathology in various conditions including those with strong involvement of T-cells. These include, for example, infection (bacterial, parasitic, fungal, viral), malignancy, kidney and other transplants, skin disorders (e.g. atopic dermatitis, psoriasis), granulomatous disease (e.g. sarcoidosis), lung diseases (e.g. idiopathic pulmonary fibrosis, ARDS, asthma), autoimmune disease characterised by chronic inflammation (e.g. rheumatoid arthritis, SLE, diabetes), myocardial infarction (CP-10 may contribute to the reperfusion damage associated with release of inflammatory mediators from neutrophils), and thrombosis (neutrophil products may be involved in recanalisation of blocked vessels).

Accordingly, CP-10 or analogues, mutants, fragments or derivatives of CP-10 may be used to alter the inflammatory capacity or metabolism of mammalian cells. Similarly, these compounds or antibodies or antagonists thereto, particularly antibodies to the chemotactic domain of CP-10, may be useful anti-inflammatory agents.

Since CP-10 is associated with delayed-type hypersensitivity reactions and is responsible for similar histopathology when injected intradermally it has potential therapeutical applications. First, a composition comprising an antibody to CP-10 may be administered to a patient undergoing a delayed-type hypersensitivity reaction, for example one with a contact allergy to heavy metals, such as gold, or to agents such as poison ivy. Secondly, a non-functional antagonist may be used for this purpose. Alternatively, CP-10 or peptides thereof may be used in patients who are immunocomprised—such as those with AIDS, or those undergoing immunosuppressive therapy, to attract phagocytes to, and to activate phagocytes at sites of infection such as the pneumocystis—infected lung.

In addition, as a number of chronic inflammatory conditions are characterised by a localised high concentration of phagocytic cells, the administration of antibodies against CP-10 may inhibit inflammation and therefore provide the basis for their therapeutic use. This would apply to such conditions as autoimmune disease such as rheumatoid arthritis, systemic lupus erythamatosis, coeliac disease, multiple sclerosis, Guillian Barre syndrome, autoimmune thyroiditis, rejecting grafts, tumours, etc. In general, monoclonal antibodies or non-functional analogues or antagonists of CP-10 may be used in disease currently treated using steriod therapy.

Occupancy of receptors of chemoattractants on phagocytes initiates cellular responses that are essential for normal host defence and wound healing. Intracellular signals generated by chemoattractant receptor occupancy are capable of regulating gene expression, such as of the oncogenes c-fos and c-myc, to produce distinct modulatory signals. All chemoattractants known to date interact initially with a receptor molecule on the cell surface which initiates these events. Non-functional analogues or antagonists of CP-10 may suppress chronic inflammation by inhibiting CP-10 receptor binding. Binding of CP-10 to its receptor would be the trigger for the cellular responses including chemotaxis.

Thus, in a further aspect of the present invention, there is provided a pharmaceutical composition comprising CP-10, or an analogue, mutant, fragment or derivative thereof, or an antibody thereto in association with a pharmaceutically acceptable carrier or diluent. The active component of such a pharmaceutical composition may of course either be derived from natural sources or be prepared by synthetic or recombinant DNA techniques. Antibodies may be prepared by known techniques as described in greater detail hereinafter.

Cystic fibrosis (C.F.) is the most common lethal genetic syndrome among white children and is also the cause of much of the chronic progressive pulmonary disease encountered in children. Early features of lung disease in C.F. are of an inflammatory nature and are non-infective. The majority of cells infiltrating the lung are PMNs and many appear to be dead or degenerating. C.F. antigen comprises about 20% of the total cytoplasmic protein of neutrophils and is responsible for calcium binding to yield the typical turbidity characteristic of C.F. saliva. C.F. antigen (MRP8, 14) is also present in inflammatory macrophages. The function of these proteins is unclear although they may be involved in the killing of pathogens. CP-10 may be involved in recruitment and activation of PMNs in the lung in C.F.

Furthermore, it has been suggested that the inflammatory lung disease, critical in patients with cystic fibrosis, may be mediated by proteases. These patients have low levels of serum protease inhibitors (indicating binding with active protease) and tissue damage similar to that believed to occur in lungs of patients with emphysema by proteolytic enzymes, is proposed (33).

Accordingly, in view of the proteolytic activity of CP-10, therapeutic intervention by CP-10, by analogues of CP-10 or of the active site of the protease, by specific protease inhibitors or by antibodies to CP-10 or to the active site may be possible. These reagents may be useful, not only to control inflammation and tissue damage in inflammatory conditions, but also to cystic fibrosis and emphysema.

As broadly described above, the present invention extends to analogues, mutants, fragments and derivatives of CP-10. Suitable analogues include chemically modified CP-10-like peptides, and the term "analogues" is used herein to include any functional chemical equivalent of CP-10 or fragments thereof which has CP-10-like properties and activity. Analogues contemplated herein include, but are not limited to modifications to side chains, incorporation of non-natural amino acids and/or their derivatives during peptide synthesis, and the use of cross-linkers or other conformational constraints during synthesis. Suitable mutants include, for example, mutants of the murine CP-10 sequence set out above or the human or other mammalian equivalent thereof, in which single or multiple amino acids are added or deleted or replaced by different amino acids. Fragments of CP-10 include, for example, fragments of the murine CP-10 sequence set out above or the human or other mammalian equivalent thereof, comprising at least 10 and preferably at least 20 consecutive amino acids. Particularly preferred fragments are those based on or corresponding to the amino acid "hinge" or "variant" region of the murine CP-10 sequence between amino acids $Pro^{42}$ and $Arg^{55}$. Derivatives of CP-10 include, for example, derivatives of the murin CP-10 sequence set out above or the human or other mammalian equivalent thereof, wherein amino and/or hydroxyl functions are glycosylated.

The present invention further extends to homo- and hetero-dimers of CP-10 wherein the two CP-10 moieties or one CP-10 moiety and a heterologous peptide are bound together, for example through an intermolecular S-S bridge or by non-covalent binding. Once again, the CP-10 moiety may, for example, be murine CP-10 having the sequence set out above or the human or other mammalian equivalent thereof.

The present invention also extends to antibodies, both polyclonal and monoclonal, or fragments thereof or specific binding moieties based on the structure of immunoglobulin, reacting with CP-10 as well as antagonists of CP-10. In particular, in this aspect the invention includes such antibodies directed to murine CP-10 having the sequence set out above or to the human or other mammalian equivalent thereof, or to peptide epitopes thereof. The antibodies may also be directed to the analogues, mutants, fragments or derivatives or CP-10 as described above.

Such antibodies or antagonists may be used to alter the chemotactic activity of CP-10, to alter the proteolytic activity of CP-10, to purify CP-10 by affinity chromatography, or they may be used as diagnostic reagents to detect CP-10 in body fluids such as urine, blood, serum, plasma, in cultures of mammalian cells, or in tissue sections.

The chemotactic factor CP-10 of this invention, or analogues, mutants, fragments or derivatives thereof, as described herein may be synthesized by solid phase peptide synthesis or other known chemical techniques for peptide synthesis. Alternatively, "recombinant" CP-10 or mututants, fragments or derivatives may be prepared by use of he recombinant DNA techniques which are now well known and widely used. Both chemical synthesis and preparation by recombinant DNA techniques provide means whereby analogues, mututants, fragments and derivatives can be readily prepared, as well as CP-10 itself. Preparation of these compounds by recombinant DNA techniques will usually comprise the steps of:

(a) isolating a DNA coding for the desired compound or a fragment thereof from a cDNA or a genomic DNA library of murine or human cells and optionally mutating it, or chemically synthesising such a DNA, (b) incorporating the DNA into an appropriate expression vector, (c) transferring the obtained hybrid vector into a recipient host, (d) selecting the transformed host from untransformed hosts by culturing under conditions under which only the transformed host survives, (e) culturing the transformed host under conditions which allow expression of the heterologous polypeptide, and (f) isolating the desired compound, mutant, fragment or derivative thereof, and, if required, derivatizing the obtained compound, mutant or fragment thereof.

Purification of murine CP-10 from a murine MPIF preparation, and techniques for production of recombinant CP-10 are described above. CP-10 of human or other mammalian origin may be identified by techniques which are well known in the art.

For example, by purification of stimulated human lymphoid cells or of cell lines of culture supernatants or other human cells to homogeneity using procedures similar to those described using open and high performance liquid chromatography or by affinity of human CP-10 to antibodies to murine CP-10 which may cross-react with the human equivalent. Confirmation of amino acid sequence by N-terminal sequence analysis of the intact molecule and of fragments thereof may be carried out as described for murine CP-10. Alternatively, positive clones may be identified from human cDNA libraries on the basis of hybridisation with oligonucleotide probes prepared from the murine CP-10 sequence, particularly according to the amino acid sequence of the novel "hinge" region sequence of murine CP-10 as described herein. Preparation of human CP-10 by recombinant DNA techniques using DNA from such positive clones is described above.

Comparative testing of the chemotactic activity of full length murine CP-10 and a peptide corresponding to the "hinge" region of CP-10 (CP-10$_{42-55}$) has revealed that the smaller peptide has similar chemotactic potency to full CP-10.

Accordingly a further aspect of the invention relates to a chemotactic peptide of amino acid sequence (SEQ ID NO: 2, SEQ ID NO: 3, as follows) Pro-Gin-Phe-Val-gin-Asn-Ile-Asn-Ile-Glu-Asn-Leu-Phe-Arg(-Tyr) and derivatives, functional homologues, mutants or substitutions thereof. This peptide has chemotactic activity for neutrophils, monocytes/ macrophages or other mammalian cells.

The following Examples and accompanying drawings illustrate the steps and procedures used in the purification and characterisation of murine CP-10 in accordance with this invention. In the drawings:

Figure 1A:
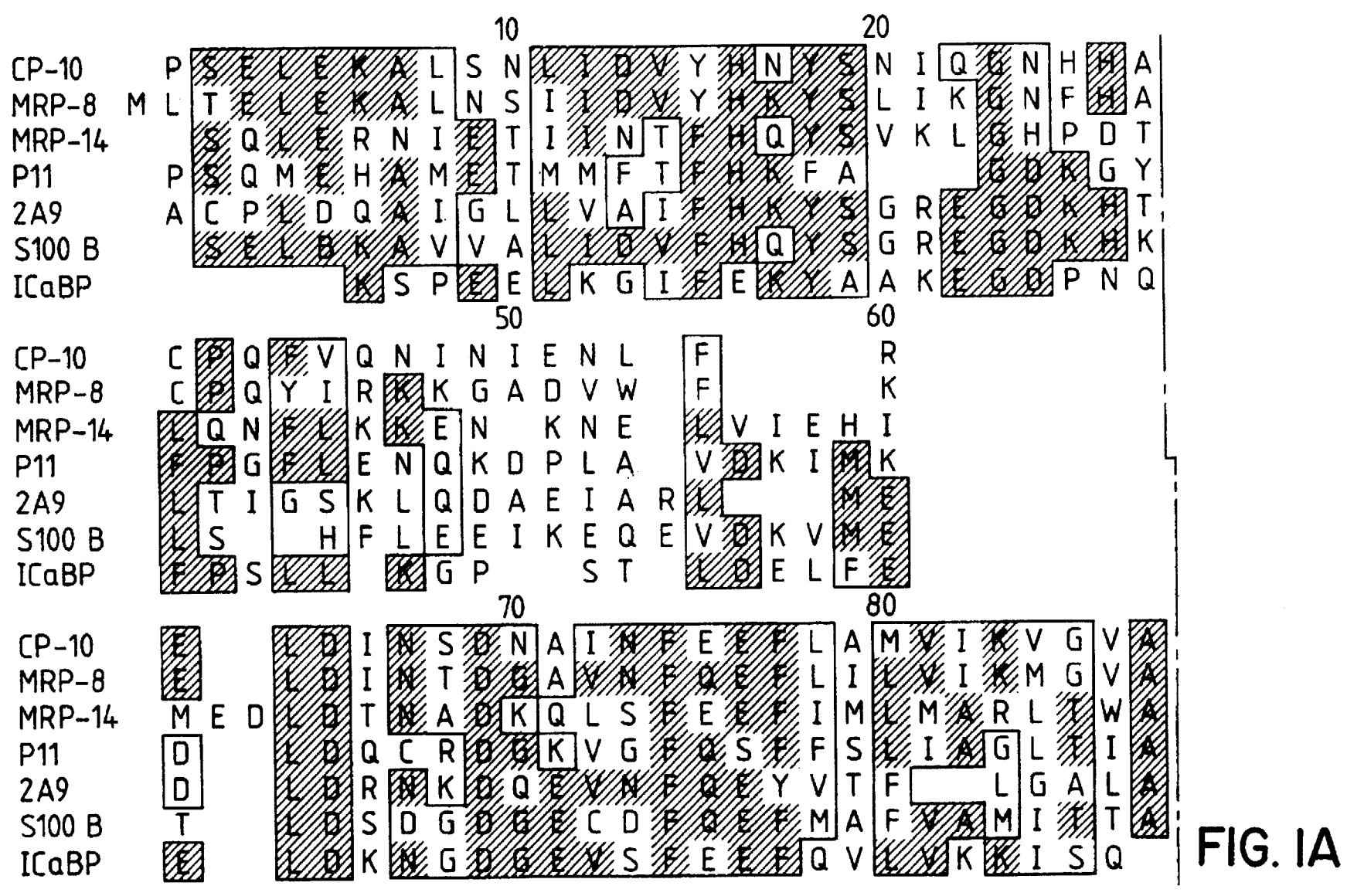

FIG. 1A and 1B, taken together, are a comparison of amino acid sequences of CP-10 (SEQ ID NO: 1) and various S-100 (SEQ ID NO: 7 through SEQ ID NO: 12, respectively) proteins.

Alignment of the amino acid sequences (single letter amino acid code) was achieved by introducing a minimal number of short gaps into individual sequences. Conserved regions between at least three of the S-100 proteins are boxed. Regions of absolute similarity are shaded. Regions typical for calcium binding domains of S-100 proteins (position 19–32 and 62–73) and the N-terminals are highly conserved in all S-100 proteins (22).

FIG. 2A, 2B and 2C, taken together are is a comparison of the amino acid and nucleotide sequence of full length murine CP-10 (SEQ ID NO: 4, and SEQ ID NO: 6, respectively) and hMRP8 (SEQ ID NO: 16 and SEQ ID NO: 23, respectively).

FIG. 3 shows a C$_4$-RP-HPLC profile of CP-10.

Con A stimulated spleen cell supernatant was concentrated and purified by cation exchange, Cu$^{++}$ affinity and Cu$^{++}$ PolyCatA mixed batch MPLC as described in steps 3.1, 3.3.1, 3.2.1, 3.3.2 and applied to reversed-phase HPLC on a Bakerbond C$_4$-WP HPLC column. Aliquots of 1 min fractions were assayed for chemotactic activity. Absorbance at 214 nm (–) and chemotactic activity of peak fractions in 0.1% (lighter boxes) and 0.5% (darker boxes) aliquots is shown.

FIG. 4 shows a size exclusion HPLC profile of CP-10.

A preparation of CP-10, purified on reversed phase HPLC (C$_4$-RP-HPLC, step 3.2.3) was subjected to gel filtration HPLC on a TSK G3000SW column and tested for chemotactic activity as described in step 3.2.4. Aliquots of fractions (0.5%) are used at 1:2 (darker boxes) and 1:4 (lighter boxes) dilution. References proteins chromatographed under the same conditions provide a m. wt. calibration curve; 1: OVA (44 kD), 2: soybean trypsin inhibitor (20.1 kD), 3: cytochrome C (12.4kD), 4: aprotinin (6.5 kD).

FIG. 5A and 5B show shows C$_8$-RP-HPLC profiles of CP-10.

Homogeneous CP-10 obtained by rechromatography of material with chemotactic activity from S.E. HPLC (FIG. 3) on analytical C$_8$-RP-HPLC (*) is injected onto microbore C$_8$-RP-HPLC. Peaks A and B are collected manually and each subjected to chemotaxis assay (step 1). Hatched bars represent chemotactic activity of peaks A and B.

FIG. 6 shows gel electrophoresis of CP-10.

Aliquots of CP-10 preparations, which were homogeneous as judged by HPLC on an Aquapore RP300 HPLC column (step 3.2.6) were subjected to Tricine-SDS PAGE on a 16.5% polyacrylamide gel under reducing conditions (5% β-mercaptoethanol) as described (35). Electrophoresis was carried out for 18 h at 90 V and gels were silverstained according to Heukeshofen and Dernick (36).

The Figure represents mounted photographs of two gels: Janes 1–3, dilutions of molecular weight marker proteins (14.4–90.0 kD, Pharmacia); lane 1, CP-10 purified as described in steps 3.1–3.2.3, 3.2.5 (C$_8$RP-HPLC) and 3.2.6; lane 2, CP-10 purified as described in steps 3.1–3.2.4 and 3.2.6; lanes 4–6, dilutions of molecular weight marker peptides (2.4–17.2 kD, Pharmacia).

FIG. 8 shows the partial amino acid sequence of murine CP-10 obtained by chemical sequencing and the various peptides used in obtaining the sequence (SEQ ID NO: 17 through SEQ ID NO: 23, respectively).

Chemotactic protein eluting from SE-HPLC was applied to a C$_8$ Aquapore HPLC cartridge and eluted with a gradient of CH$_3$CH (–). Homogenous CP-10 was collected manually according to the absorbance at 214 nm (–) and diluted serially for chemotaxis assays using murine neutrophils. Mean values (●) of a representative experiment are shown (inset to the figure). Chemotactic activity of 5% EAMS (○) is given for comparison.

Figure 10A:
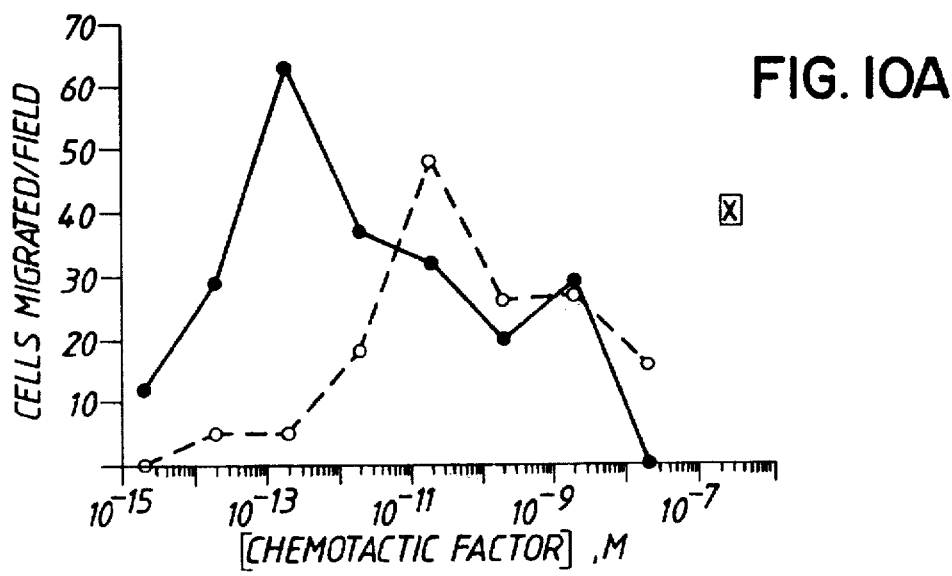
Figure 10B:
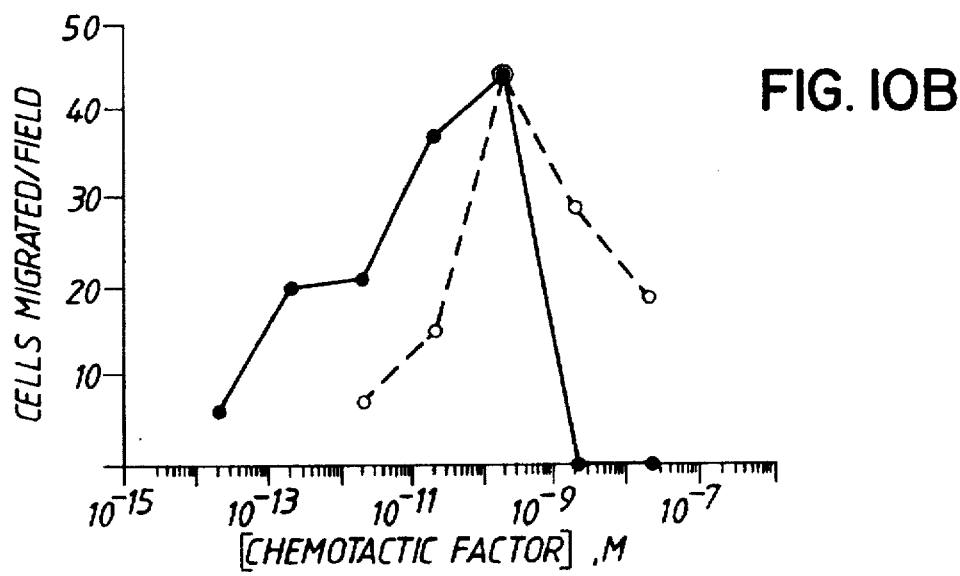
Figure 10C:
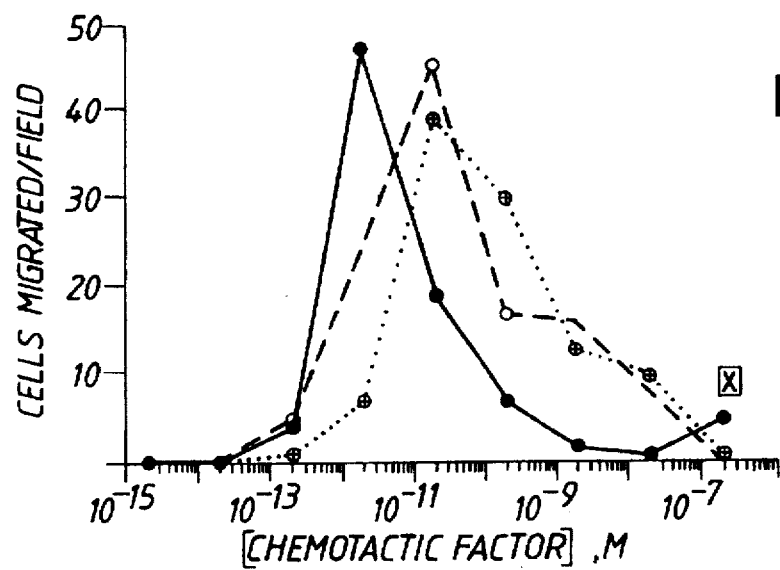

FIG. 10 illustrates the chemotactic response of murine and human cells to CP-10 and derived peptide, CP-10$_{42-55}$. Homogeneous CP-10 obtained from C$_8$RP-HPLC (step 3.2.6) and synthetic CP-10$_{42-55}$ were diluted 10 fold between $10^{-7}$ and $10^{-15}$M into RPMI 1640 containing 0.1% BSA and tested for chemoattractant activity. Murine PMN (Panel A), human PMN (Panel B) and murine mononuclear cells or a murine monocytoid cell line, WEHI 265 (Panel C) were used as efffector cells. The chemotactic response to native CP-10 (—●—) and CP-10$_{42-55}$ (—○—) was compared to the chemotactic activity of 5% EAMS (panel A,X) or $10^{31}$ $^7$M FMLP (panel C,X). In addition, murine macrophages were tested for their response to CP-10$_{42-55}$ (panel C, --○--).

FIG. 11 shows overexpression of mCP10 in *E. coli* using pGEX expression system.

EXAMPLE 1

Step 1. Measurement of bioactivity

Aliquots of chromatography fractions without organic solvents are diluted directly with RPMI 1640 (Gibco, Grand Is. N.Y.) before assay. To remove organic solvent prior to assay, fractions (5–100 μl) are freeze-dried in the presence of 2 μg of albumin (calbiochem; 5× crystalline) and reconstituted to the original volume with RPMI 1640. Samples to be stored before testing are kept at 31 70°C., preferably in the solvent used for elution.

CP-10 associated MPIF activity is measured as described by J. Ryan and C. Geczy, (16). Chemotaxis of mouse polymorphonuclear leukocytes (PMN) is measured as described by Falk et al. (34) Briefly, PMN are obtained from the periotoneal cavity 1 day after ip injection with thioglycollate broth. Chemotaxis is assayed in a 48-well microchemotaxis chamber (Neuro Probe Inc., Bethesda, Md.). The upper wells contain wells (2.5×10$^4$) in 50 μl RPMI 1610 serum albumin (BSA; Calbiochem). The lower wells contain separated fractions diluted in RPMI 1640 with 5% FCS or 0.1% BSA. The upper and lower chambers are separated with a PVP-free polycarbonate membrane (Nucleopore, 5 μm; Neuroprobe). The chamber is incubated for 1.5–2 hr at 37° C. after which the filter is removed, air dried and stained. Migrating cells are quantitated over 5 microscope fields (×40 objective) using Image Analysis (Wild-Leitz, Lane Cove, Australia).

Step 2. Preparation of the CP10-containing supernatant

Spleen cells from QS-mice isolated and cultured for 24 hr with Sepharose-4B bound Concanavalin A. (Pharmacia, North Ryde, Australia) and the cell supernatant is harvested as described earlier by C J Ryan and C. Geczy, (14). Prior to storage at −70° C. supernatants are adjusted to 0.1 μg/ml DNAse, 0.1 μg/ml RNase (Boehdringer Mannheim, North Ryde, Australia), 0.01% Tween-20(Sigma) and 0.25 mM phenylmethylsulphonyl fluoride (PMSF, Sigma).

Batches of 5-6 1 supernatant are concentrated to 150–200 ml and dialysed against 0.05M NaCl in buffer A (0.02M Tris-HCl, 0.01% Tween-20, 0.25 mM PMSF, pH:6.5) using a spiral ultrafiltration cartridge (mol. weight cut off: 10, 000D, Amicon Scientific, Australia).

Step 3. Isolation and Purification of CP10

Step 3.1 Heparin-Sepharose affinity chromatography

The concentrated supernatant is centrifuged at 10,000 g 4° C. for 30 min and loaded at a flow rate of 18 m/h, 4° C. (peristaltic Minipuls 3-pump, Gilson) onto a column (16× 160 mm) of Heparin Sepharose 6B (Pharmacia) equilibrated in buffer A. The column is washed with 0.05M NaCl and with 0.2M NaCl in buffer A until the absorbance at 280 nm (UV-detector 115, Gilson reaches background levels and bound material is eluted with a NaCl gradient (total vol. 100 ml) of 0.2–1M NaCl in buffer B (0.02M Tris-HCl, pH:6.8) at a flow rate of 7 m/h. Fractions of 2.5 ml are collected and aliquots of individual fractions assayed at 5% and 2.5% (v/v) for bioactivity. CP-10 associated with macrophage procoagulant inducing factor (MPIF) elutes in two peaks between 0.6 and 0.9M NaCl (14,16).

Step 3.2 High Performance Liquid Chromatography (HPLC) Nonmetallic "Waters 650 Advanced Protein Purification System" equipped either with a Waters 484 Tunable Absorbance Detector or a Waters 490 Programmable Multiwavelength Detector and a Gilson 202 Fraction Collector are used for all MPLC an HPLC separations. Unless otherwise stated, samples were loaded onto columns by using an HPLC pump and one of the four solvent lines of the HPLC system. After sample load the same solvent line is used to pump equilibration buffer through the HPLC system until the absorbance reaches the baseline level of the solvent in use.

Step 3.2.1. Zinc-, Copper-Affinity Chromatography

Step 3.2.1.1 Preparation of $Zn^{++}$ and $Cu^{++}$ Affinity Medium Pressure Liquid Chromatography (MPLC) columns Suspensions of iminodiacetic acid (IDAA) immobilized on TSK-HW 65F gel particles (Pierce, Rockford, Ill., USA) are incubated with solution, of 1 mg/ml $ZnCl_2$ or 1 mg/ml $CuSO_4$ for 30 min at r/t and fines are removed from the gel slurry as described by the manufacturers (Fractogel TSK catalog, E. Merck, F.R.G.) Gel-bound chelates of zinc and copper in $H_2O$ are packed at constant flow (3 ml/min) into individual glass columns (10×100 mm; Waters Advanced purification −1 glass columns, Millipore/Waters, Lane Cove, Australia) and the columns are washed subsequently with each 200 ml $H_2O$ and 2M NaCl in buffer B at 3 ml/min.

Step 3.2.1.2. $Cu^{+30}$ Affinity MPLC

The pooled fractions of Step 3.1. are adjusted to 2M NaCl and pumped at a flow rate of 3 ml/min onto a Zn++ and a Cu++-affinity column in sequence (equilibrated at 2M NaCl in buffer B), beginning with the Zu++-affinity column. When the absorbances at 280 nm reaches baseline levels, the columns are disconnected and bound material eluted separately with a ternary gradient of 0.1M to 1.0M NaCl and 0.00M to 0.05M imidazole in Buffer B at a flow rate of 3.25 ml/min. Fractions are collected every minute and aliquots of individual fractions testes at 5% and 2.5% for bioactivity. MPIF-associated chemotactic activity elutes only from the $Cu^{++}$-affinity MPLC column at a buffer composition of 0.02M imidazole, 0.1M NaCl in buffer B.

Step 3.2.2. High resolution cation exchange HPLC

Pooled fractions from step 3.2.1.2. are diulted four fold with $H_2O$ and loaded at 1.5 ml/min onto a Bakerbond Wide-Pore CBX HPLC column (4.6×250 mm, JT. Baker, Phillipsburg, N.J., USA) equilibrated with 0.05M NaCL in 0.02M Tris-HCl, pH 6.5. Bound proteins are eluted with a 0.05–0.5M gradient of NaCl in 0.02M Tris-HCl pH 6.5–7.0.

The absorbance of the eluate is monitored at 280 nm and 1 min fractions collected automatically. Aliquots assayed at 5% and 10% (v/v) revealed bioactivity between 0.25 and 0.035M NaCl.

Step 3.2.3. Reversed-phase HPLC on butyl wide pore silica

Figure 1B:
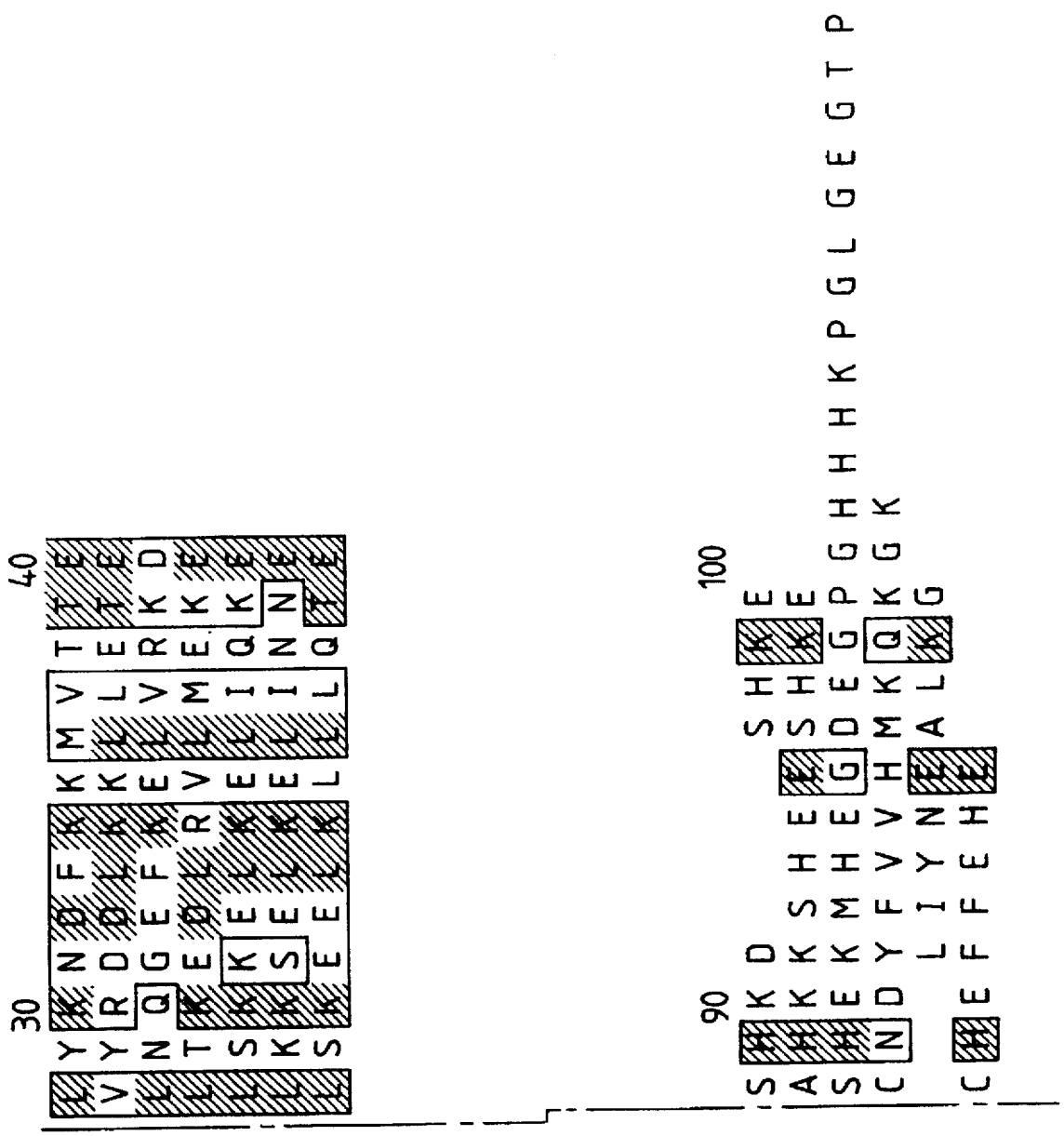
Figure 3:
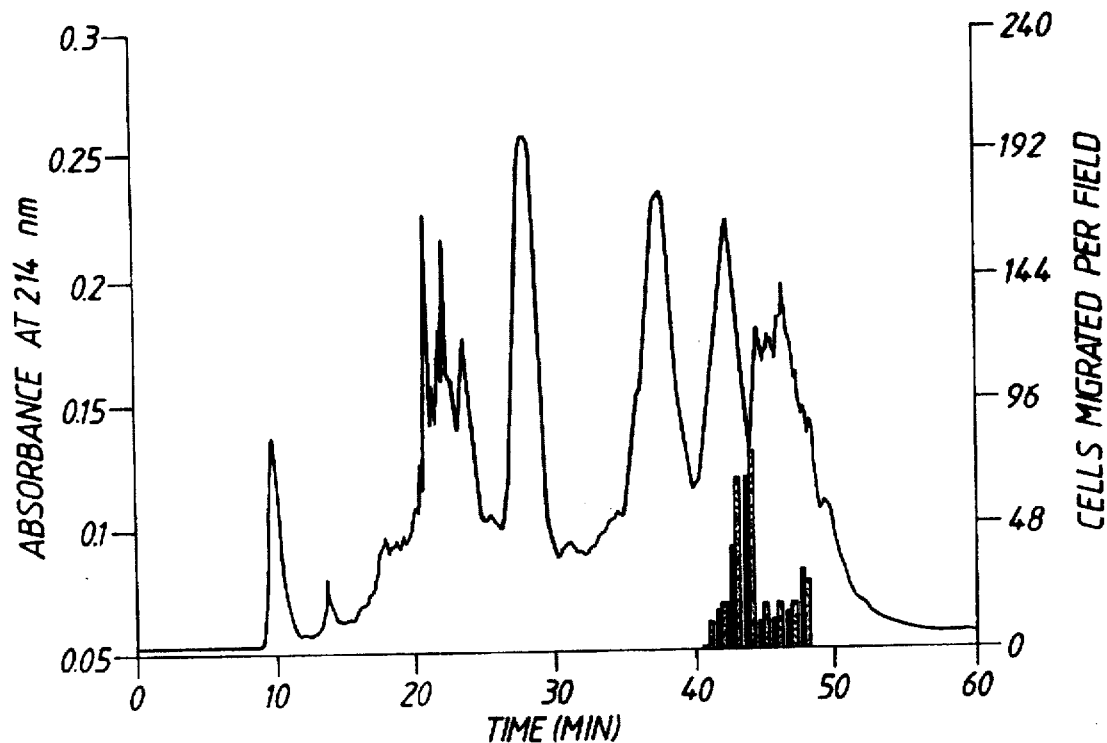

Pooled material from step 3.2.2. (having specific activity) is adjusted to 0.1% TFA and loaded onto a Bakerbond C4-wide pore HPLC column (4.6×250 mm), equilibrated in 80% Solvent C and 20% solvent D; solvent C is 0.1% TFA in water and solvent D is 80% acetonitrile, 0.1% TFA in water. After 5 min at this solvent composition proteins are eluted with a three-step gradient of solvent D is solvent C ranging from 20% to 40% D in 10 min followed by 40% to 50% D in 20 min and 50% to 100% D in 20 min. Aliquots (0.5%) of individual 1 min fractions are assayed for chemotactic activity and reveal peak activity eluting with 49.4% solvent D (39.5% acetonitrile) as part of a complex peak eluting with 52% solvent D (41.6% acetonitrile). The absorbance profile and chemotactic activity of relevant fractions is shown in FIG. 3.

Step 3.2.4. Size exclusion HPLC

Peak fractions of step 3.2.3. are concentrated to 50 µl, using a "Speed Vac" Concentrator (Savant), adjusted to 40% acetonitrile, 0.1% TFA in water and injected via a Model 9125 Rheodyne sample injector (Rheodyne, Calif., USA) onto a TSKG 3000 SW high performance gel filtration column (7.5×300 mm, LKB) equilbrated with 40% acetonitrile, 0.1% TFA in water at 0.5 ml/min. Fractions are collected manually according to the absorbance profile of the eluate at 214 nm and 0.5% aliquots of individual fractions diluted to 50, 25 and 10% are tested for chemotactic activity.

Figure 4:
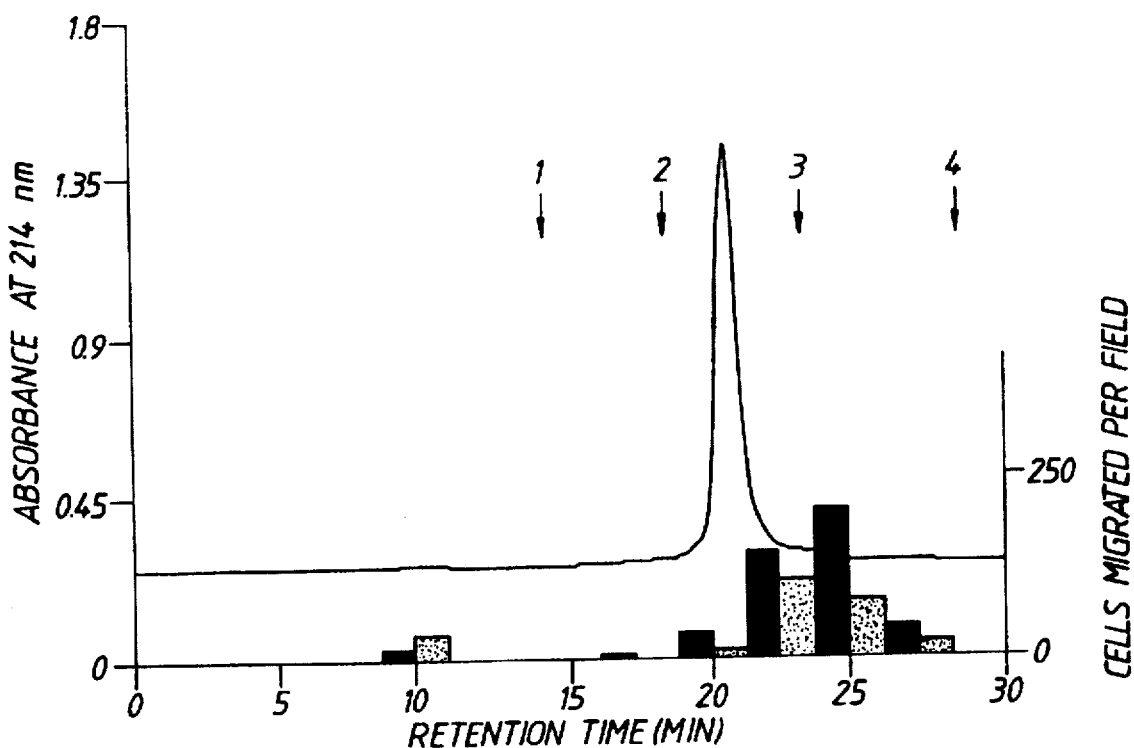

As shown in FIG. 4 CP-10 is eluted with an apparent molecular weight of 10.3 kD, when compared to standard molecular weight markers aprotinin (6.5 kD), cytochrome C (12.4kD), soybean trypsin inhibitor (20.1 kD) and ovalbumin (44 kD).

Step 3.2.5. Reversed-phase HPLC on octadecyl wide-pore silica

As an alternative to the separation on size exclusion HPLC (3.2.4.) pooled material from step 3.2.3. is diluted 4× with aqueous 0.1% TFA and loaded on to a Bakerbond $C_{18}$- wide pore HPLC column (4.6×100 mm; J T. Baker), equilibrated at 1 ml/min in 68% solvent C and 32% solvent D. A two step gradient of solvent D in solvent C is applied 10 min followed by 59%–70% D in 30 min. CP-10 elutes with 49.7% acetonitrile in 0.1% aqueous TFA (62.1% solvent D), with a purity of approximately 90% as judged by SDS-Tricine PAGE (35) and silverstaining (36).

Step 3.2.6. Reversed-phase HPLC on octyl wide-pore silica

Analytical and microbore reversed-phase $C_8$ HPLC is performed on Aquapore RP300 Cartridges (4.6×100 mm and 2.1×100 mm, 7 µm silica, Applied Biosystems, Foster City, Calif., USA) equilibrated in 100% solvent C. Preparations of CP10 from step 3.2.4. or 3.2.5. are diluted 4 fold with solvent C and loaded in multiple 1 ml injections via the Rheodyne injector onto the HPLC cartridge.

The flow rate for loading a sample onto the analytical cartridge is 1.5 ml/min and onto the microbore cartridge is 0.15 ml/min. A gradient of 1% /min acentronile in solvent C over 60 min is started 5 min after last injection. The flow rate on the analytical cartridge is kept at 1 ml/min, on the microbore cartridge at 0.1 ml/min and eluting material is collected manually according to the absorbance at 214 nm.

Figure 5A:
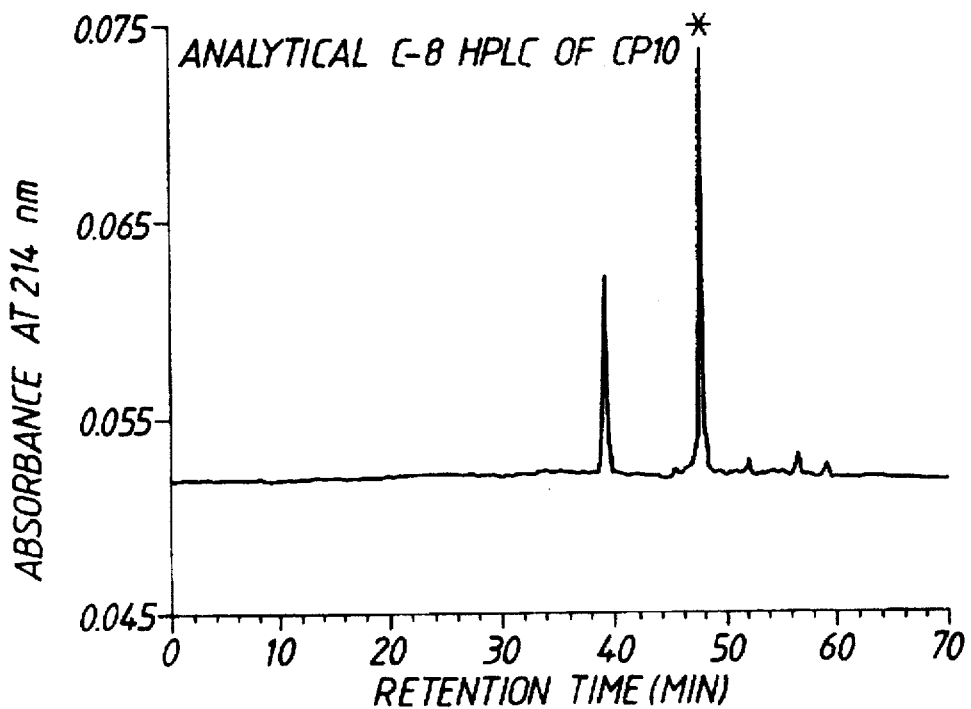
Figure 5B:
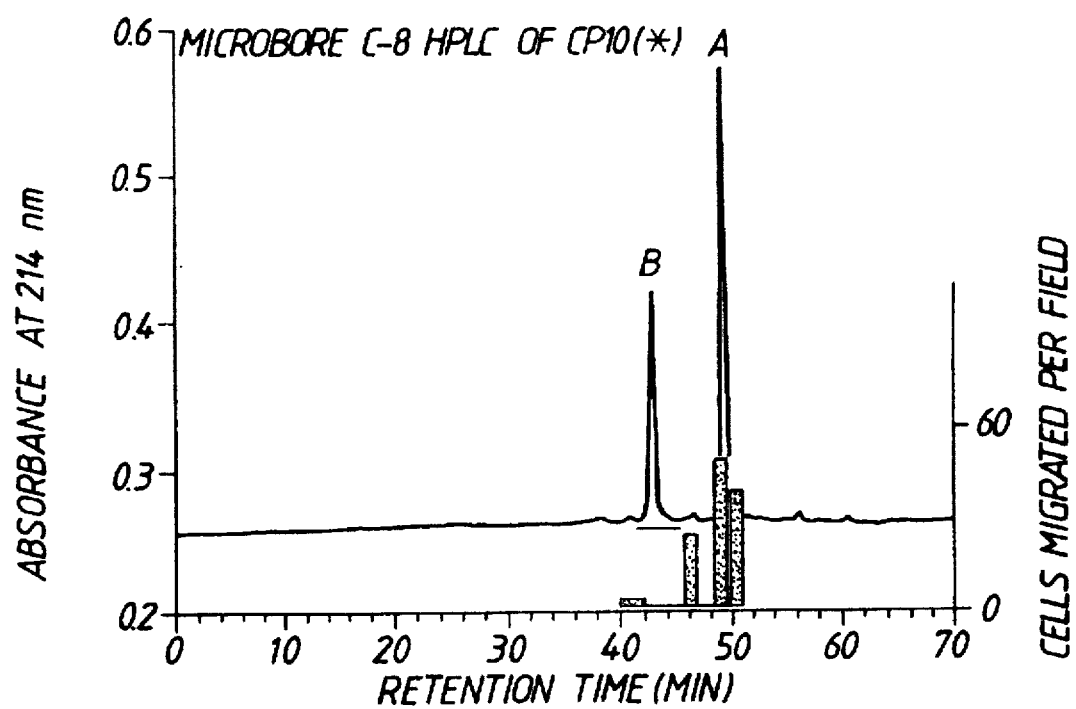

FIGS. 5A and 5B show shows that CP-10 elutes as a symmetrical peak with retention times of 47.7 min and 49.2 min (equivalent to 47.5% acetonitrile) from the analytical and the microbore $C_8$-HPLC cartridges respectively. This preparation has chemotactic activity in the range $10^{-12}$—$10^{-13}$M.

Figure 6:
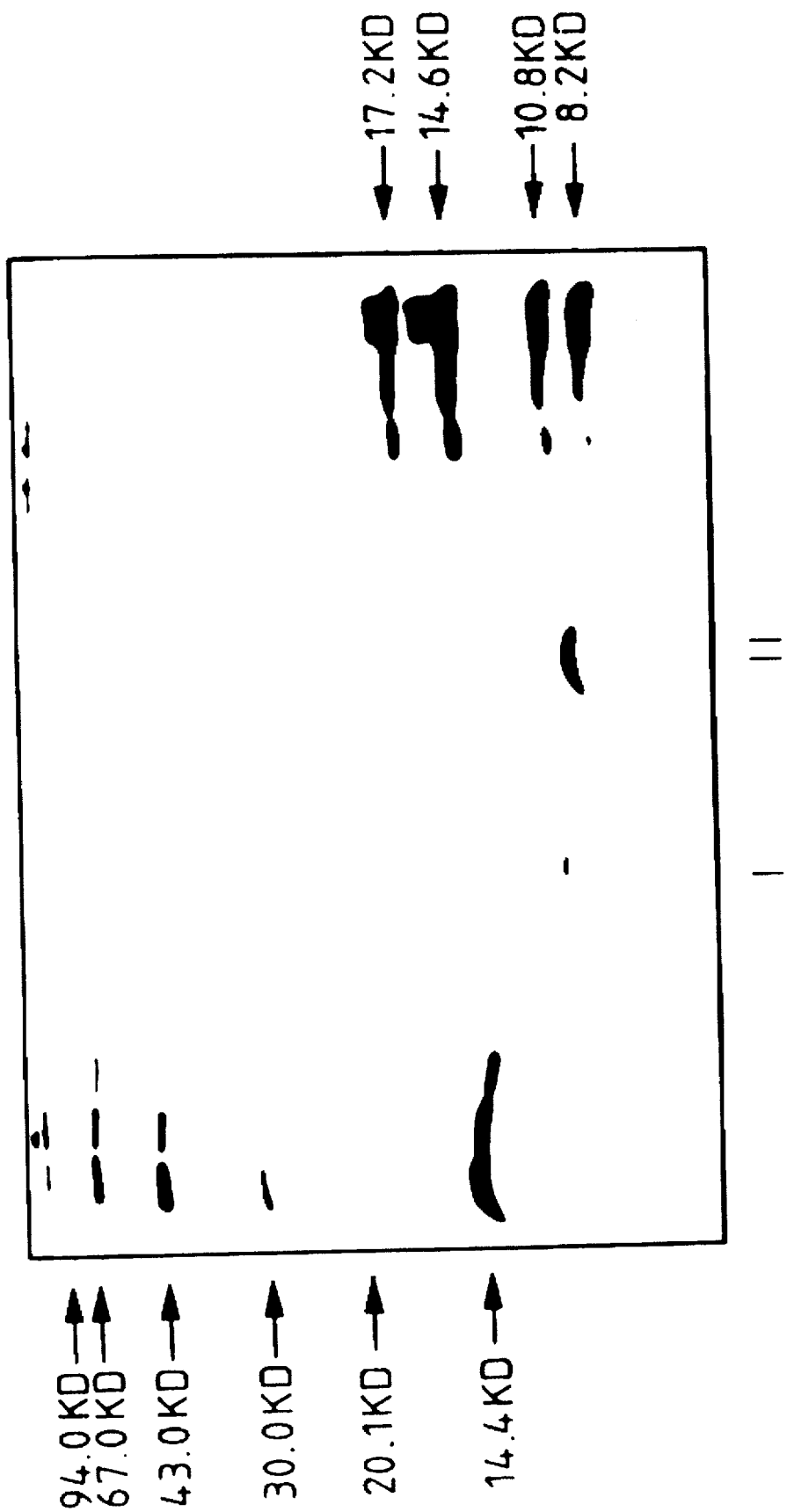

Analysis on silverstained (36) SDS-Tricine PAGE under reducing conditions (5% β-mercaptoethanel) of CP-10 purified in steps 3.2.5. and 3.2.6. reveals a predominant band at 10 kD (more than 95%) and a minor band at 65 kD. Material purified in steps 3.2.4 and 3.2.6. reveal the same predominant band at 10 kD and a minor band of 14 kD as shown in FIG. 6.

Step 3.3. Alternative method of purifying CP10 from concentrated supernatants of Con A stimulated murine spleen cells.

Step 3.3.1. Cation exchange HPLC on Poly (Aspartic Acid)—Silica

The crude supernatant of step 1 is centrifuged at 10,000 g, 4° C. for 30 min and proteins are separated on a column (10×300 mm, Advanced Purification-1 glass column, Millipore/Waters) of Poly CAT A (polyaspartic acid) silica (Poly LC, Columbia, Md., USA). The column is packed using a slurry of the silica particles (15–20 µm diameter, 30 nm pore size) in 100% isopropanol under constant flow as described in step 3.2.1.1.

For chromatography of CP10 the column is equilibrated with 0.02M Tris, pH 6.5 at 3 ml/min and washed with this buffer after loading of the sample until the absorbance 280 nm reaches baseline levels.

Bound material is eluted at 3 ml/min using a gradient of 0–0.5M NaCl in Tris-HCl, pH 6.5–7.0 over 40 min and the absorbance monitored at 280 nm. Fractions are collected automatically every min and assayed for bioactivity.

Material eluting in the range from 0.17–0.33M NaCl was pooled for further purification.

Step 3.3.2. Mixed Mode HPLC on IDAA-Cn$^{++}$ TSK/Poly Cat A-Silica

The pooled material from step 3.3.1. is adjusted to 2M NaCl and separated on IDAA-Cu$^{++}$ affinity HPLC as described in 2.2.2. Proteins eluting with 0.02M imidazole/ 0.1M NaCl are collected manually and diluted fourfold with buffer B for mixed mode HPLC.

A 10×100 mm Advanced purification 1- glass column (Millipore/Waters) is packed under constant flow with a 1:1 mixture of IDAA-Cu$^{++}$TSK65F and Poly Cat A-silica in 3M sodium acetate as packing solvent. The column is equilibrated at 2.25 ml/min with buffer B and the sample is loaded at this flow rate following the procedure described in 3.2.1.1.

The column is washed with 0.6M NaCl in buffer B (5 min at 2.25 ml/min), buffer B (5 min at 2.5 ml/min), 0.02M imidazole/0.06M NaCl in buffer B (10 min at 2.5 ml/min) and buffer B (10 min at 2.5 ml/min). Bound material is eluted with a binary gradient of 0.06–1.0M NaCl and 0.0–0.05M imidazole over 40 min at a flow rate of 2.5 ml/min. Fractions are collected every minute and aliquots assayed at 2.5% and 5% for CP-10 associated bioactivity.

Proteins eluting in the range of 0.24M NaCl/0.01M imidazole and 0.4M NaCl/0.02M imidazole were adjusted to 0.1% TFA for chromatography on C4-RP-HPLC (step 3.2.3.).

Step 3.4. Cyanogen bromide cleavage and peptide mapping on RP-HPLC

Homogeneous CP-10, obtained as manually collected fractions from Step 3.2.6—(approx. 2.5 µg) in 48% acetonitrile in buffer C, 0.02% Tween 20 is lyophylized to near dryness (10 µl) and resuspended to 100 µl with 70% formic acid. Cyanogen bromide (2.5 mg) is added under nitrogen, the tube sealed and incubated in the dark at 25° C. for 20 h. The peptide mixture is diluted 50 fold with $H_2O$ and injected in 1 ml portions onto an Aquapore RP300 cartridge (2.1×100 mm. ABI), equilibrated at 0.5 ml/min with 100% solvent C. Elution of peptides is achieved at 0.1 ml/min as described in step 3.2.6 and peptides are collected manually according to the absorbance at 214 nm.

Step 3.5. Trypsin digestion and peptide mapping on RP HPLC

Step 3.5.1. Preparation of murine S-carboxymethyl-CP-10 (Cm-CP-10)

CP-10 (5 µg) in 120 µl 35% aqueous acetonitrile containing 0.1% (v/v) trifluoroacetic acid ($F_3AcOH$; 99% pure, Pierce Chemical Co., Rockford Ill., USA) and 0.02% Tween 20 (Pierce) is concentrated to approximately 10 µl by centrifugal centrifugation (Savant, Ind. Hickville, N.Y.), diluted to 160 µl with 7.5M guanidine HCL (Sequenal grade, Pierce) containing 0.2M Tris-HCl buffer, pH8.5, 0.002M EDTA and 0.02% (v/v) Tween 20 and then reduced with dithiothreitol (Calbiochem La Jolla, Calif., USA; 0.015M) at 40° C. for 4.5. h. Alkylation is achieved by the addition of iodacetic acid (puriss grade, Fluka, Buchs, Switzerland; final concentration, 0.05M) to the mixture and incubation continued for 30 min at 25° C. in the dark. The reaction is halted by addition of 25 µl of 2-mercaptoethanol. Cm-CP-10 is recovered from the mixture using a reversed-phase high-performance liquid chromatography (RP-HPLC) procedure previously described by Simpson et at (37). The Cm-CP-10 containing fraction (60 µl) is adjusted to 0.02% (v/v) with respect to Tween 20 and then diluted to 1 ml with 1% (w/v) $NH_4HCO_3$ (containing 0.02% (v/v) Tween 20) prior to enzymatic digestion.

Step 3.5.2. Trypsin digestion

Cm-CP-10 (4 µg) in 1 mol 1% (w/v) $NH_4HCO_3$, pH 7.8 containing 0.001M $CaCl_2$ and 0.02% (v/v) Tween 20 is digested with 0.5 µg trypsin (treated with tosylphenylethylchloro-methane; Worthington Biochemical Co. N.J., USA) for 16 hrs at 37° C.

Step 3.5.3. Purification of polypeptides by high-performance liquid chromatography instrumentation Peptide mixture resulting from trypsin digestion are fractionated by reversed-phase HPLC on a Hewlett-Packard liquid chromatograph (model 1090-A)-fitted with a diode-array detector (model 1040A) as described (37) employing a low-pH ($F_3AcOH$, pH2.1) mobile phase and a gradient of acetonitrile.

Figure 7:
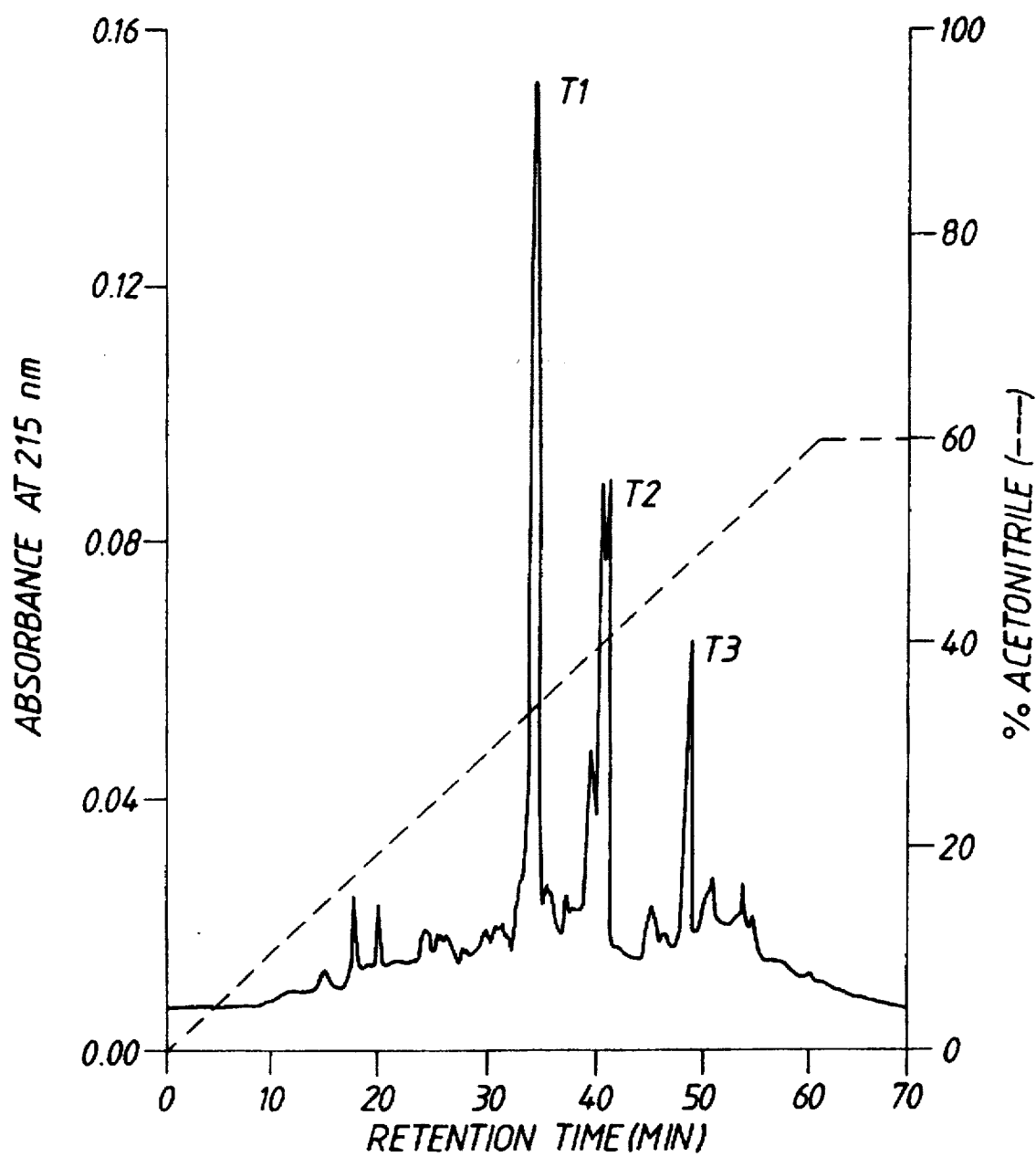
FIG. 7 is a graphic illustration of the microbore RP-HPLC separation of peptides of Cm-CP-10 derived from digestion with trypsin.

Reversed-phase fractionation of these digests, however, results in a complex pattern of peptide-containing peaks (FIG. 7). All of the peptide fractions from the first dimension RP-HPLC are subjected to a second chromatographic step using the same chromatographic support and acetonitrile gradient but a different mobile phase (e.g., unbuffered sodium chloride or 20 mM sodium phosphate, pH 7.0). For some peptides a third chromatographic step is necessary before a homogeneous peptide is isolated. In the latter situation, an ODS-hypersil column and a different organic solvent (methanol) are used (37).

Column support used for the purification of Cm-CP-10 and derived peptides is Brownlee RP-300 (300 nm pore size, 7 µm particle diameter, octylsilica packed into a stainless steel column 100×2.1 mm i.d; Brownlee Laboratories, Santa Clara, USA).

Step 3.5.4 Peptide nomenclature

The following prefixes are used to denote the origin of various peptides T, Trypsin, CN, Cyanogen bromide. Peptides are numbered in the order of their positions in the final sequence.

Step 3.6. Amino acid sequence analysis

Automated Edman degradation of protein and peptides is performed using Applied Biosystems sequencers (models 470A and 477A) equipped with on-line phenylthiohydantion (Pth) amino acid analyzer (model 120A). Total Pth-amino acid derivatives from the sequencer are injected onto the liquid chromatograph using a modified sample transfer device as described (38). Polybrene (39) is used as a carrier.

Figure 8:
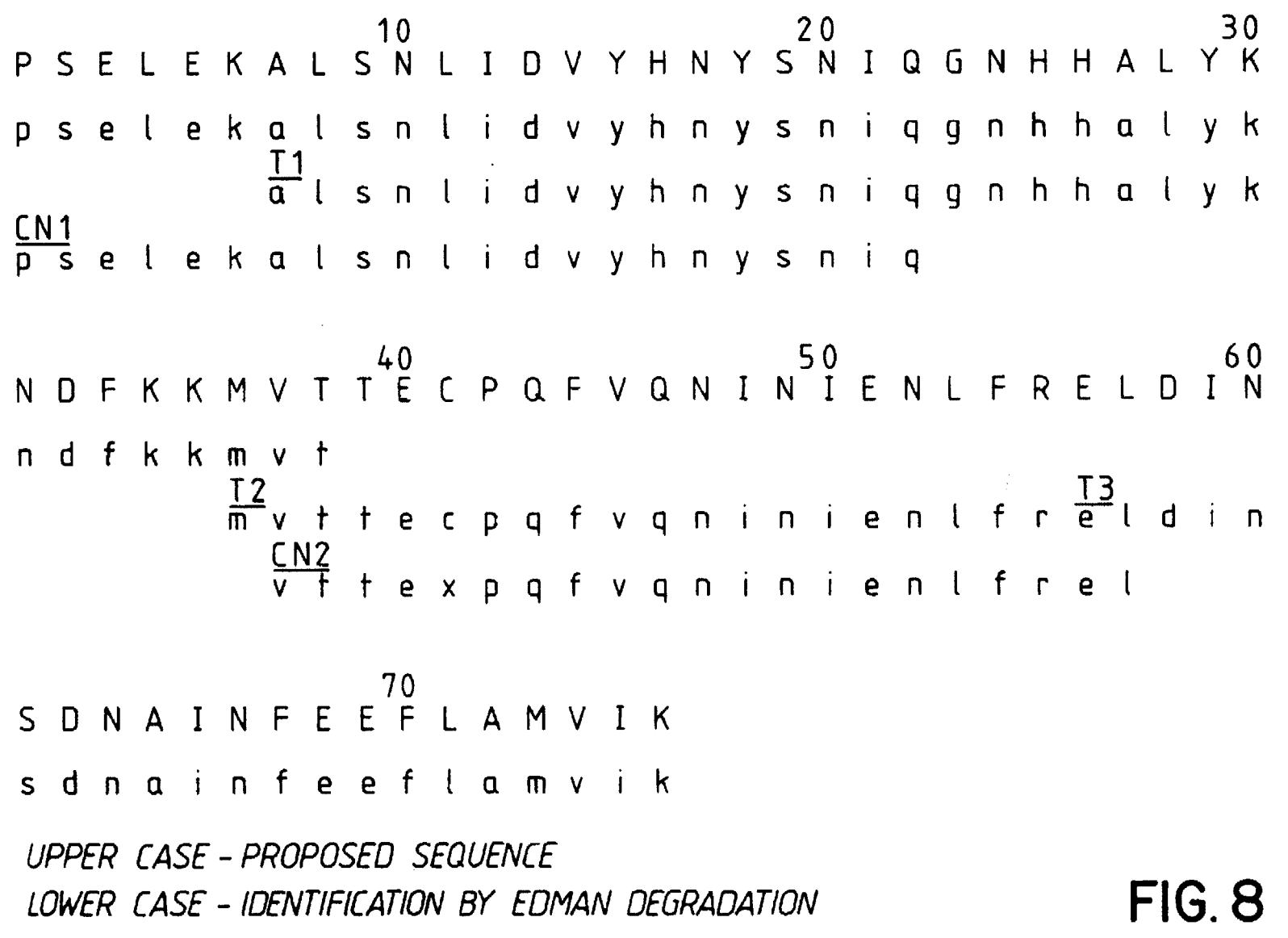

Partial amino-acid sequence of CP-10 and trypsin and cyanogen bromide-derived peptides is given in FIG. 8.

Step 4. Demonstration of proteolytic activity of CP10

Step 4.1. Degradation of Ovalbumno by $^{125}$I-CP10

Step 4.1.1 Radioiodination of CP10

Because homogeneous CP-10 is poorly soluble in aqueous buffers the iodination with protocol Enzymobeads (BioRad Australia) as suggested by the manufacturers is modified as follows:

A preparation of CP10, purified to apparent homogeneity as described in Steps 3.1 to 3.2.6. and with a mass of approximately 2 µg is iodinated with 1 mm Ci $NaI^{125}$ (Amersham Australia) using 0.05/0.1 ml of the Enzymobead Radioiodination Reagent (single reaction vial; Bio Rad).

The RP-HPLC purified peptide is freeze dried in a "Speed-Vac" Concentrator, reconstituted into 0.05 ml of 60% acetonitrile in Solvent C and adjusted to 0.2M sodium phosphate buffer, pH 7.2 in a total volume of 0.1 ml. Enzymobeads and $Na^{125}I$ are added and the reaction is started with 0.025 ml β-D-glucose (1% in 0.2M phosphate buffer, pH 7.2). After 15 min the mixture is transferred to a conditioned (as instructed by the manufacturer) 5 ml-$C_4WP$-SPE cartride (J T. Baker) and washed with 25 ml of Solvent C. Bound material is eluted with 3×0.8 ml of 60% acetonitrile in Solvent C and injected in 1 ml-aliquots onto an equilibrated (100% Solvent C) Bakerbond $C_{18}$-WP HPLC column (4.6×100 mm J T Baker), bound material is eluted with a gradient of 1%/min acetonitrile in solvent C over 60 min., and fractions are collected every minute into tubes (Nune immunotubes, Medos, Victoria Australia) containing 10 µg ovalbumin (OVA) and then freeze dried. Aliquots (0.01 ml) of individual fractions are counted in a γ- counter (LKB) and analysed by SDS-Tricine PAGE and autoradiography to confirm the molecular weight of the radiolabelled protein. $^{125}$I-CP10 is stored in aliquots of approx. 4×10$^5$ cpm in the presence of 0.01 mg OVA in 0.15M NaCl, 0.02M Tris pH; 7.2 (TBS) at −80° C.

Step 4.2.1 Assessment of proteolytic activity of $^{125}$I-CP10

Radioiodinated CP10 in the presence of ovalbumin is analysed for proteolytic activity by S. E. HPLC and SDS-Tricine-PAGE, silverstaining and autoradiography. Chromatography and calibration of the TSK 300 SW column (7.5× 300 mm, LKB) is performed as described in step 3.2.4.

Prior to injection onto the S.E. HPLC column an aliquot of $^{125}$I-CP10 (approx. 4×10$^6$ cpm equiv. to 1.5% of the total preparation, step 4.1.1), is adjusted to 40% acetonitrile in solvent C. One half of this sample is injected onto the HPLC column after 2 h at r/t, the eluate is collected manually according to the absorbance at 214 nm and radioactivity of the load and individual fractions quantitated in a γ- counter.

Gel sample buffer, (0.05 ml/0.05M Tris, 4% SDS, 12% [w/v] glycerol, 0.002% bromophenol blue, pH 6.8) is added to the second half of the sample and to individual fractions and the volume is reduced to 0.05 ml in a Speed-Vac concentrator. The samples are adjusted to 5% β-mercaptoethanol and incubated for 1 h at 56° C. prior to electrophoresis according to Schagger and von Jagow (35).

Molecular weight marker proteins (14.4–90.0 kD, 2.6–17.2 kD; Pharmacia) and OVA (subjected to S.E. HPLC under the same conditions as described above) are loaded in parallel lanes onto the same gel. After electrophoresis the gel is silverstained and autoradiographed for 55 h using a Kodak X-Omatfilm.

Analysis on S.E. HPLC reveals three peaks with apparent molecular weights of 1:15 kD, II:12.5 kD, III:11.5 kD containing I:22.8%, II:21.5% and III:6.8% of the injected radioactivity. No absorbance is seen in the elution position of ovalbumin. Analysis of peak I on SDS-Tricine PAGE shows a single band at 44 kD by silverstain and a single band at 10 kD by autoradiography. Peak II and III reveal multiple bands ranging from 67–2.6 kD by silverstaining only minor bands at 44 kD are visible, the equivalent fraction not subjected to size exclusion reveal bands ranging from 90–14.5 kd with a predominant band in the position of ovalbumin.

Quantitation of autoradiography of this lane using a Hoefer GS-300 Scanning Densitometer (Hoefer Scientific Instruments, San Francisco, Calif.) and a GS-370 Data System for the integration of peaks reveals 18.7% of the radioactivity (gaussian integration of peak area) in the migration position of CP10 and 11.7% in the migration of OVA. The predominant radioactivity (52.5%) is associated with bands ranging from 30 to 14.4 kD.

The distribution of radioactive bands in similar in the lane loaded with peak II from the S.E. HPLC: 13.1% and 6% of the radioactivity is associated with the positions of CP-10 and OVA respectively, while the major portion is distributed over the molecular weight range from 30–14.4 kD. Although there is a discrepancy between the elution position of proteins on S.E. HPLC and the band pattern on SDS-Tricine PAGE, these results indicate degradation of OVA in the presence of $^{125}$I-CP-10.

EXAMPLE 2

1. Method of Chemotaxis Measurement

Triplicate samples (in RPMI 1640 and 0.1% serum albumin) to be tested are pipetted into the low wells of a Neuro Probe 48 well micro-chemotaxis chamber (Neuro Probe Inc. Md., USA) in a total vol. of approx. 25 µl. Wells are covered with a Nuclepore PC membrane (PVP free, 5 µM) and upper chambers filled with cell suspension (1–1.5× $10^4$ cells in 50 µl RPMI 1640 containing 0.1% albumin). Chambers are incubated for various times depending on the cells being tested (90 min. for neutrophils, 3 hr. for macrophages) at 37° C. in an atmosphere of 5% $CO_2$ in air. Membranes are removed and wiped free of excess cells on the "cell" side of the membrane.

Cells are fixed in methanol and stained with Wright's stain or Coomassie blue. Destined membranes are placed on microscope slides and held in place with a thin layer of microscopic immersion oil. Cells which have migrated through the pores of the membrane are quantitated by measuring the total cell area per 5 microscope fields using an Image Analysis system. The chemotactic activity was tested in the following cell types: mouse macrophages and neutrophils; human neutrophils and mononuclear cells.

2. Preparation of CP-10 Peptide

A synthetic peptide of the sequence proline-glutamine-phenylalanine-valine-glutamine-asparagine-isoleucine-asparagine-isoleucine-glutamic acid-asparagine-leucine-phenylananine-aginine-tyrosine comprising the unique "hinge" region of CP-10 from amino acids $Pro^{42}Arg^{55}$ was prepared by standard techniques. A C-terminal tyrosine was added so that it could be used as a radioiodinated tracer.

Amino acid code-$p^{42}$ QFVQNINIENLFR$^{55}$Y (SEQ ID NO: 4)

3. Preparation of CP-10 and CP-10$_{42-55}$ Test Solution

Purified CP-10 and CP-10$_{42-35}$ were stored in 35% acetonitrile/0.1% TFA in water and were diluted to 0.1% BSA in RPMI 1640 to yield 10-fold dilutions between $10^{-8}$–$10^{-13}$M.

4. Preparation of Murine Macrophages

Murine macrophages are elicited by ip injection of thioglycollate broth 3 days before harvesting by peritoneal lavage and cells are tested in chemotaxis assays as outlined above. Alternatively, a murine monocytoid cell line, WEHI 265, grown in continuous cell culture can be used as effector cells.

5. Measurement of Vascular and Dermatological Changes in Rat Skin

Purified CP-10 and CP-10$_{42-55}$ were injected subcutaneously into Sprague-Dawley rats. Small sections of skin from treated rats were removed and subjected to microscopic examination after fixing and staining with Haemotoxyline Eosin.

RESULTS

Effect of Murine Cells

Figure 9:
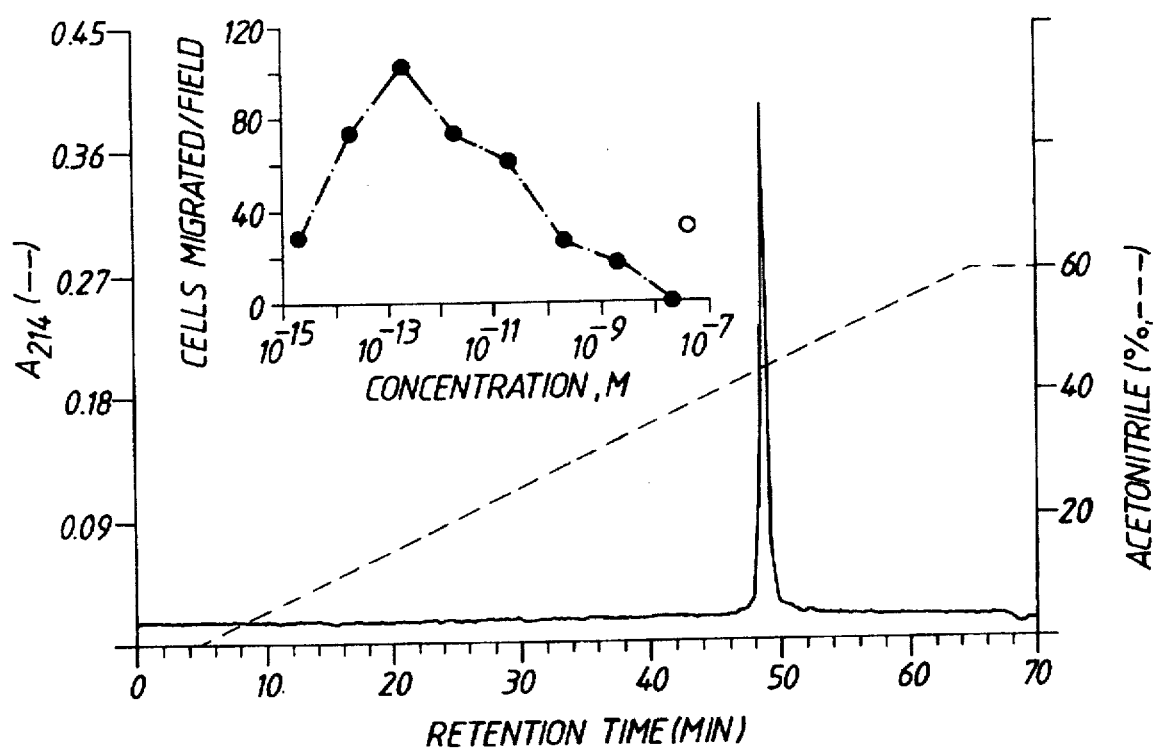
FIG. 9 shows the C$_8$ RP-HPLC of CP-10 and titration of chemotactic activity.

Full length CP-10 was chemotactic for mouse neutrophils to $10^{-14}$M with peak activity at $10^{-13}$M (FIG. 9).

CP-10$_{42-55}$ was chemotactic for mouse neutrophils to $10^{-12}$M with peak activity at $10^{-11}$M.

Full length CP-10 was found to be chemotactic for murine macrophages to $10^{-13}$M with peak activity between $10^{-11}$–$10^{-12}$M. CP-10$_{42-55}$ was chemotactic for murine macrophages with peak activity at $10^{-11}$M.

Effect on Human Cells

Full length CP-10 was found to be chemotactic to human blood neutrophils to at least a concentration of $10^{-13}$M. Peak activity was at $10^{-11}$M.

CP-10$_{42-55}$ was chemotactic for human blood neutrophils to at least a concentration of $10^{-11}$M. Peak activity was at $10^{-10}$M.

Full length CP-10 was found to be chemotactic for human peripheral blood mononuclear cells to at least a concentration of $10^{31}$ $^{11}$M. Peak activity was not determined.

CP-10$_{42-55}$ was found to be chemotactic for human peripheral blood mononuclear cells to a concentration of at least $10^{31}$ $^{11}$M. Peak activity was not determined. (A comparison of the activities of full length CP-10 and CP-10$_{42-55}$ on human and mouse cells is shown in FIG. 10.)

Determination of Full Length cDNA Sequence of Murine CP-10

Figure 2C:
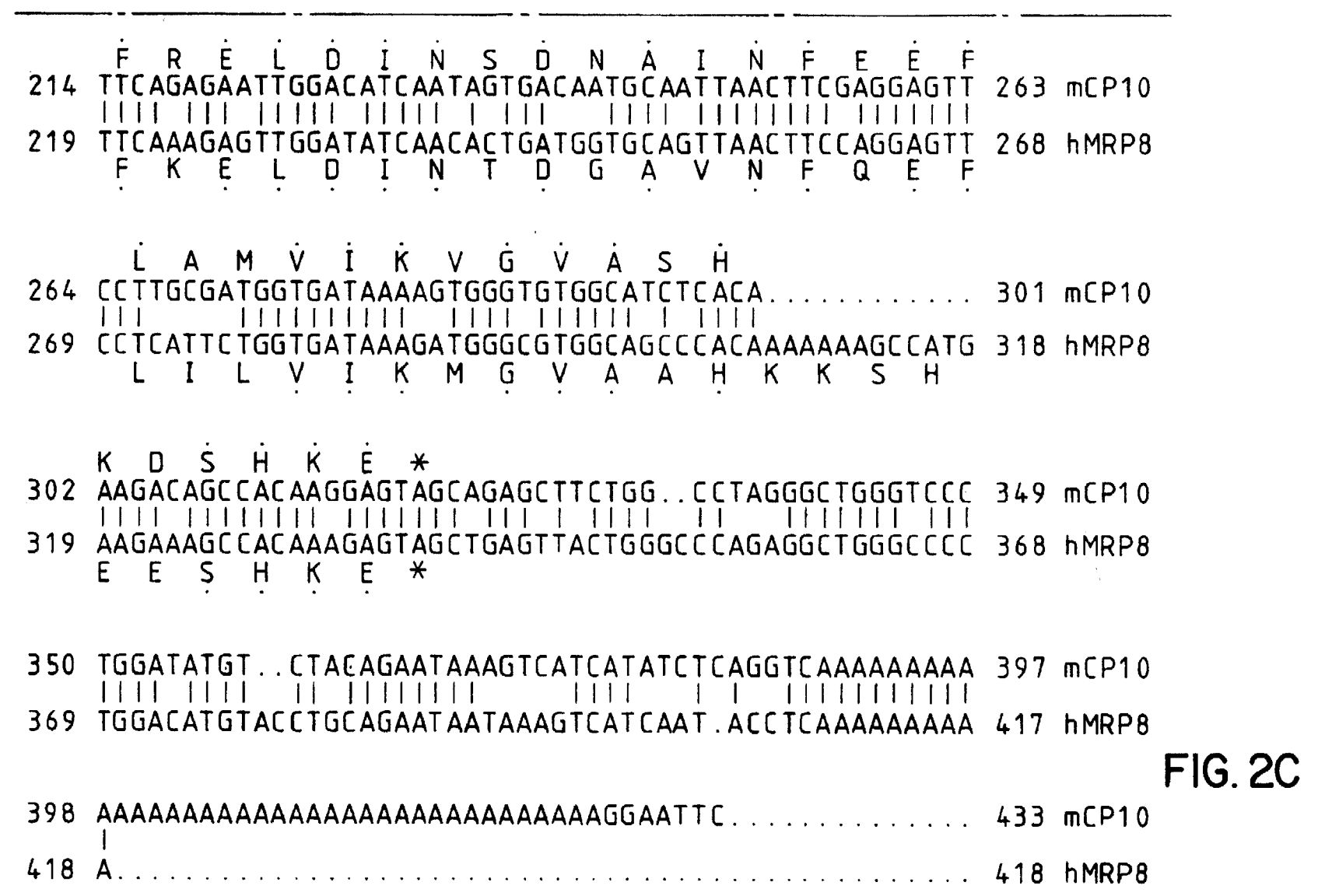

The cDNA sequence of murine CP-10 is given in FIGS. 2A, 2B and 2C, taken together. The mCP10 cDNA was derived from a Sepharose-Concanavalin A-activated spleen cell library prepared using cells from A/J mice.

The mCP10 cDNA isolate is a γgt10 recombinant with a 430 bp EcoRI insert. The insert was subcloned in both orientation into the 2.7 kb vector pUCI119 to yield recombinants 10/pUC119 (mCP10 cDNA 3' to 5' with respect to universal sequencing primer) and 12/pUC 119 (mCP10 cDNA 5' to 3' with respect to universal sequencing primer). The DNA sequence of mCP-10 was determined on both strands.

The cDNA sequence of CP-10 is given (FIGS. 2A, 2B and 2C) together with human MRP8 for comparison. These proteins show 69.6% homology at the DNA level. The full length amino acid sequence of CP-10 is given as (SEQ ID NO: 1)

PSELEKALSN$^{10}$LIDVYHNYSN$^{20}$IQGNHHALYK$^{30}$N
DFKKMVTTE$^{40}$CPQFVQNINI$^{50}$ENLFRELDINSDN$^{60}$
AINFEEF$^{70}$LAMVIKVGVA$^{80}$SHKDSHKE$^{88}$

The amino acid sequence deduced from the cDNA sequence is in full agreement with sequence pro$^1$-lys$^{76}$ obtained by amino acid sequencing of the N-terminal, trypic and cyanogen bromide peptide fragments derived from purified CP-10. Sequence val$^{77}$-glu$^{88}$ representing the C-terminal end of the molecule is new data obtained by cDNA sequencing.

Thus CP-10 is an 88 amino acid protein with a calculated mass of 10.163D. Isoelectric point as determined by computer analysis of amino acid sequence was 5.5. In addition to the amino acid sequence differences between mCP-10 and hMRP8, the cDNA sequences reveal an alignment gap in the CP-10 sequence between his$^{88}$ and lys$^{83}$ when compared with the MRP8 amino acid sequence (SEQ ID NO: 5 and SEQ ID NO: 6, as follows)

| mCP-10 | —A S H$^{82}$ * * * * K$^{83}$ D S H K E |
| hMRP8  | —A A H$^{82}$ K K S H E$^{87}$ E S H K E |

MRP8 has an additional 4 amino acids (12 base pairs) not present in CP-10. (see FIGS. 2A, 2B and 2C).

Vascular and Dermatological Changes in Rat Skin

Examination of microscopic sections of rat skin following administration of full length CP-10 or peptide corresponding to CP-10$_{42-55}$ revealed accumulation of neutrophils and increased vascular permeability revealing the potent chemotactic activity of these peptides. Native CP-10 induced a response over 24 hr which comprised neutrophils and mononuclear cells and was similar to that of a delayed-type hypersensitivity reaction, CP-10$_{42-55}$ induced a shorter-lived response which was optimal after 6–8 hr indicating differences in the abilities of these agents to attract phagocytic cells in vivo.

EXAMPLE 3

Expression of Recombinant CP-10

CP-10 has been overexpressed in *E. coli* using the pGEX expression system (40). Two different CP-10 overexpression constructs have been produced: pCP12 contains the CP-10 coding region cloned into the Bam HI site of pGEX-2T; pCP10 contains a Factor Xa cleavage site followed by the CP-10 coding region cloned in the Eco RI site of pGEX-IN. Both constructs have been verified by double-stranded DNA sequencing.

The level of CP-10 overexpression in this system has been evaluated by purifying fusion proteins from crude cell-free lysates by affinity chromatography on immobilised glutathione and analysed using SDS-PAGE in accordance with the manufacturer's directions (Glutagene, Trade Mark of AMRAD Corporation Limited). FIG. 11 shows expression of these fusion proteins as follows:

lane 1: affinity purified GST expressed from pGEX-IN;
lane 2: affinity purified GST-Xa-mCP10 fusio in protein expressed from pCP10;
lane 3: affinity purified GST expressed from pGEX-2T;
lane 4: affinity purified GST-T-mCP10 fusion protein expressed from pCP12.

It is estimated that the yield of the two GST/CP-10 fusion proteins is ~5 ug/ml culture. The GST/CP-10 fusion protein containing the thrombin cleavage site has been successfully cleaved with thrombin to release r-CP-10 and will be purified from cleavage products by methods similar to those described above.

REFERENCES

1. Snyderman R. Piek ML, Ann. Rev. Immunol. 1:257, 1984
2. Ryan, G B, Majno J, Am. J. Pathol 86:185, 1977
3. Wolpe S D, Cerami A, Faseb J. 3:2565, 1989
4. Ward P A, Rernold H G, David J R, Cell Immunol. 1:162, 1970
5. Altman L C, Kirchner H, Immunology 26:393, 1974
6. Postlethwaite A, Snyderman R, J. Immunol. 114:274, 1975
7. Cohen S, Ward P, Yoshida T, Burek C L, Cell Immunol. 9:363, 1973
8. Miura K, Shimokawa Y, Honda M, Hayashi H, Cell Immunol. 75:383, 1983.
9. Westwick J, Li S W, Camp R D, Immunol. Today 10:146, 1989
10. Hopper K E, Geczy C L, Davis W, J. Immunol. 126:1052, 1981
11. Geczy C L, Meyer P, J. Immunol. 128:331, 1982
12. Geczy C L, Farram E, et al. J. Immunol. 130:2743, 1983
13. Geczy C L, Hopper K, J. Immunol. 126:1059, 1981
14. Ryan J, Geczy C L, Immunol 137:2864, 1986
15. Ryan J, Geczy C L, Immunol. & Cell Biol. 65:127, 1987
16. Ryan J, Geczy C L, J. Immunol. 141:2110,1988
17. Bennett B, Bloom B R, Proc Natl. Acad Sci USA 59:756, 1968
18. Geczy C L, Friedrich W, de Weck A L, Cell Immunol. 19:65, 1975
19. Dorin J R, Novak M, et al. Nature 326:614, 1987
20. Andesson K B, et al. Scand. J. Immunol. 28:241, 1988
21. Odink K, Cerletti N, et al. Nature 330:80, 1989
22. Kligmann D, Hilt D C, Trends in Biochem. Sci. 13:437, 1988
23. Hogg N, Allen C, Edgeworth J, Eur. J. Immunol. 19:1053, 1989
24. van Heyningen V, Hayward C, et al. Nature 315:513, 1985
25. Ishida M, Honda M, Yoshimura T, Immunology 35:167, 1978
26. Hayashi H, Honda M, Yoshimura T, In "Macrophage Biology" (Richard S, Kojima M, Eds) Alan R Liss Inc. p. 231, 1985
27. Becker E L, Ward P A, J. Exp. Med, 125:1021, 1967
28. Ward P A, Becker E L, J. Immunol. 105:1057, 1970
29. Wilkinson P C, Bradley G R, Immunology 42: 637, 1981
30. Postlethwaite A E, Kang A H, J. Immunol. 123: 561, 1979
31. Matzner Y, Marx G, Drexler R, Eldor A, Thomb. Hoemost. 52: 134, 1984
32. Ceczy C I, Molecular Immunol. 17: 601, 1980
33. Kuzemko J A, The Lancet Feb. 26: 448: 1983
31. Falk, W. Goodwin R H, Leonard E J, J. Immunol. Methods, 33: 239, 1980

35. Schagger H, von Jagow G, Anal Biochem 166: 368, 1987
36. Heukeshofen J, Dernick R, Electrophoresis 9: 28, 1988
37. Simpson IRJ, Moritz R L, Rubira M R, Van Snick J, Biochem. 176: 107, 1988
38. Begg G S, Simpson R J, In "Techniques in Protein Chemistry", Huglli T E (Ed) Academic Press, Orlando Fla., USA 79, 1989
39. Klapper D G, Wilde C E, Capra J D, Anal. Biochem 85: 126, 1978
40. Smith D E, Johnson K S, Gene 67: 31, 1988

I claim:

1. An essentially pure CP-10 polypeptide comprising the amino acid sequence of a CP-10 protein secreted by Con A-activated mammalian spleen cells, said sequence including the sequence set forth in SEQ ID NO: 2, wherein said CP-10 protein has an apparent molecular weight of about 10 kDa as determined by reducing SDS-PAGE, comprises a hydrophobic N-terminal domain characteristic of the S-100 protein family, and is chemotactic for neutrophils and macrophages.

2. The polypeptide of claim 1, which has been isolated from a mammal.

3. A pharmaceutical composition comprising a polypeptide of claim 1 and a pharmaceutically acceptable carrier or diluent.

4. A process for preparing an essentially pure CP-10 polypeptide according to claim 1, comprising the step of subjecting a material containing said polypeptide to one or more chromatographic or affinity procedures, whereby said CP-10 polypeptide is substantially separated from other proteins.

5. An isolated nucleic acid molecule encoding a CP-10 polypeptide according to claim 1.

6. A vector comprising the nucleic acid sequence of a molecule according to claim 5.

7. A host cell transformed with the vector of claim 6.

8. A process for preparing the polypeptide of claim 1, comprising:

(a) preparing a DNA sequence coding for the chemotactic protein CP-10, said protein having an apparent molecule weight of approximately 10 kD and having chemotactic activity for neutrophils and macrophages;

(b) incorporating said DNA sequence into a vector;

(c) transforming a host cell with said vector;

(d) culturing said host cell under conditions which allow expression of said DNA sequence; and (e) purifying the peptide thereby expressed.

9. An essentially pure CP-10 polypeptide having the amino acid sequence of a CP-10 protein secreted by Con A-activated mammalian spleen cells, said sequence including the sequence set forth in SEQ ID NO: 2, wherein said CP-10 protein has an apparent molecular weight of about 10 kDa as determined by reducing SDS-PAGE, comprises a hydrophobic N-terminal domain characteristic of the S-100 protein family, and is chemotactic for neutrophils and macrophages.

10. A process for preparing an essentially pure CP-10 polypeptide according to claim 9, comprising the step of subjecting a material containing said polypeptide to one or more chromatographic or affinity procedures, whereby said CP-10 polypeptide is substantially separated from other proteins.

11. A process according to claim 4, comprising an immuno affinity purification step.

12. An isolated nucleic acid molecule encoding a CP-10 polypeptide according to claim 10.

13. An isolated oligonucleotide fragment of the nucleic acid molecule of claim 12, comprising at least 21 contiguous nucleotides present in the coding sequence of said molecule.

14. An essentially pure CP-10 peptide, wherein said peptide comprises the amino acid sequence set forth in SEQ ID NO: 2 and is chemotactic for neutrophils and macrophages.

15. An essentially pure CP-10 peptide, wherein said peptide comprises the amino acid sequence set forth in SEQ ID NO: 3 and is chemotactic for neutrophils and macrophages.

16. An essentially pure CP-10 peptide, wherein said peptide comprises the amino acid sequence set forth in SEQ ID NO: 1 and is chemotactic for neutrophils and macrophages.

17. An isolated oligopeptide corresponding to the hinge region of CP-10 and comprising the amino acid sequence set forth in SEQ ID NO: 2.

18. An isolated oligopeptide corresponding to the hinge region of CP-10 and comprising the amino acid sequence set forth in SEQ ID NO: 3.

19. An isolated nucleic acid molecule encoding a CP-10 polypeptide according to claim 14.

20. An isolated nucleic acid molecule encoding a CP-10 polypeptide according to claim 15.

21. An isolated nucleic acid molecule encoding a CP-10 polypeptide according to claim 16.

22. An isolated DNA sequence coding for a compound having or including the amino acid sequence represented in SEQ ID NO: 1.

23. An isolated DNA sequence coding for a compound having the amino acid sequence represented by SEQ ID NO: 2 or SEQ ID NO: 3.

24. An isolated DNA sequence comprising the CP-10 nucleotide sequence represented in SEQ ID NO: 13 or a fragment thereof, said fragment including the portion of the CP-10 nucleotide sequence corresponding to a CP-10 hinge region, said hinge region consisting of the region between nucleotide position 178 and position 219, inclusive.

25. A method for modulating an inflammatory response in a mammal, comprising the step of administering to said mammal a protein comprising the amino acid sequence of a CP-10 protein secreted by Con A-activated mammalian spleen cells, wherein said CP-10 protein has an apparent molecular weight of about 10 kDa as determined by reducing SDS-PAGE, comprises a hydrophobic N-terminal domain characteristic of the S-100 protein family, and is chemotactic for neutrophils and macrophages.

26. A method for modulating an inflammatory response in a mammal, comprising the step of administering to said mammal a protein having the amino acid sequence of a CP-10 protein secreted by Con A-activated mammalian spleen cells, wherein said CP-10 protein has an apparent molecular weight of about 10 kDa as determined by reducing SDS-PAGE, comprises a hydrophobic N-terminal domain characteristic of the S-100 protein family, and is chemotactic for neutrophils and macrophages.

27. A method for modulating an inflammatory response in a mammal, comprising the step of administering to said mammal a peptide comprising the amino acid sequence set forth in SEQ ID NO: 2 which is chemotactic for neutrophils and macrophages.

28. A method for modulating an inflammatory response in a mammal, comprising the step of administering to said mammal a peptide comprising the amino acid sequence set forth in SEQ ID NO: 3 which is chemotactic for neutrophils and macrophages.

29. A method for modulating an inflammatory response in a mammal, comprising the step of administering to said mammal a peptide comprising the amino acid sequence set forth in SEQ ID NO: 1 which is chemotactic for neutrophils and macrophages.

* * * * *